(12) United States Patent
Blackburn et al.

(10) Patent No.: US 11,288,761 B2
(45) Date of Patent: *Mar. 29, 2022

(54) DECENTRALIZED SYSTEM FOR VERIFYING PARTICIPANTS TO AN ACTIVITY

(71) Applicant: Scientia Potentia Est., LLC., Charleston, SC (US)

(72) Inventors: Jeremy Blackburn, Charleston, SC (US); Justin Southward, Charleston, SC (US); W. Kurt Taylor, N. Charleston, SC (US); Karl David, Charleston, SC (US); Austi Critchfield, Clearwater, FL (US); Michael Lu, N. Charleston, SC (US); Tim McVicker, Charleston, SC (US)

(73) Assignee: SCIENTIA POTENTIA EST., LLC, Charleston, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/230,911

(22) Filed: Apr. 14, 2021

(65) Prior Publication Data

US 2021/0233193 A1 Jul. 29, 2021

Related U.S. Application Data

(63) Continuation-in-part of application No. 17/176,056, filed on Feb. 15, 2021, which is a continuation-in-part
(Continued)

(51) Int. Cl.
*G06Q 50/26* (2012.01)
*G06Q 10/10* (2012.01)
(Continued)

(52) U.S. Cl.
CPC ......... *G06Q 50/265* (2013.01); *G06F 16/164* (2019.01); *G06Q 10/10* (2013.01); *G06Q 10/20* (2013.01); *G06Q 30/018* (2013.01)

(58) Field of Classification Search
CPC .. G06F 16/5854; G06F 16/51; G06F 16/5866; G06K 9/00201; G06K 9/0063;
(Continued)

(56) References Cited

U.S. PATENT DOCUMENTS 10,338,913 B2 * 7/2019 Franchitti .............. G06N 5/022
2017/0031676 A1 * 2/2017 Cecchetti ................. H04L 9/12

* cited by examiner

*Primary Examiner* — Garcia Ade
(74) *Attorney, Agent, or Firm* — Kim and Lahey Law Firm, LLC; Douglas W. Kim

(57) ABSTRACT

A computerized system for verifiably that individual is associated with an event comprising: a computer system in communication with an immutable storage; a set of computer readable instructions included in the computer system configured for: creating a first event record using a first data capture device wherein the first event record includes a first location, a first time and a first set of metadata wherein the first set of metadata includes a first digital representation of an individual, creating a subsequent event record using a second data capture device wherein the subsequent event record includes a second location, a second time and a second set of metadata wherein the second set of metadata includes a subsequent digital representation of a second individual; and, determining a timespan between the first time and the second time and determining if the timespan is consistent with the individual traveling from the first location to the second location.

21 Claims, 20 Drawing Sheets

Related U.S. Application Data of application No. 16/997,840, filed on Aug. 19, 2020, which is a continuation-in-part of application No. 16/994,585, filed on Aug. 15, 2020, now Pat. No. 11,232,652, which is a continuation-in-part of application No. 16/991,916, filed on Aug. 12, 2020, now Pat. No. 11,216,823, which is a continuation-in-part of application No. 16/876,080, filed on May 17, 2020, which is a continuation-in-part of application No. 16/810,782, filed on Mar. 5, 2020, now Pat. No. 11,216,781, which is a continuation-in-part of application No. 16/510,642, filed on Jul. 12, 2019, now Pat. No. 11,216,772, which is a continuation-in-part of application No. 16/452,076, filed on Jun. 25, 2019, said application No. 16/810,782 is a continuation-in-part of application No. 16/510,634, filed on Jul. 12, 2019, now Pat. No. 10,713,737, which is a continuation-in-part of application No. 16/452,076, filed on Jun. 25, 2019, said application No. 16/810,782 is a continuation-in-part of application No. 16/452,076, filed on Jun. 25, 2019.

(51) Int. Cl.
*G06F 16/16* (2019.01)
*G06Q 30/00* (2012.01)
*G06Q 10/00* (2012.01)

(58) Field of Classification Search
CPC ............ G06K 9/00771; G06K 9/00288; B64C 39/024; B64C 2201/127; G06Q 10/1057; G06Q 40/08; G06Q 50/08; G06Q 10/103; G06Q 10/0875; G06Q 10/109; G06Q 40/125; G06Q 50/265; G16H 40/20; H04N 9/8205; H04N 5/77
USPC ......................................................... 705/325
See application file for complete search history.

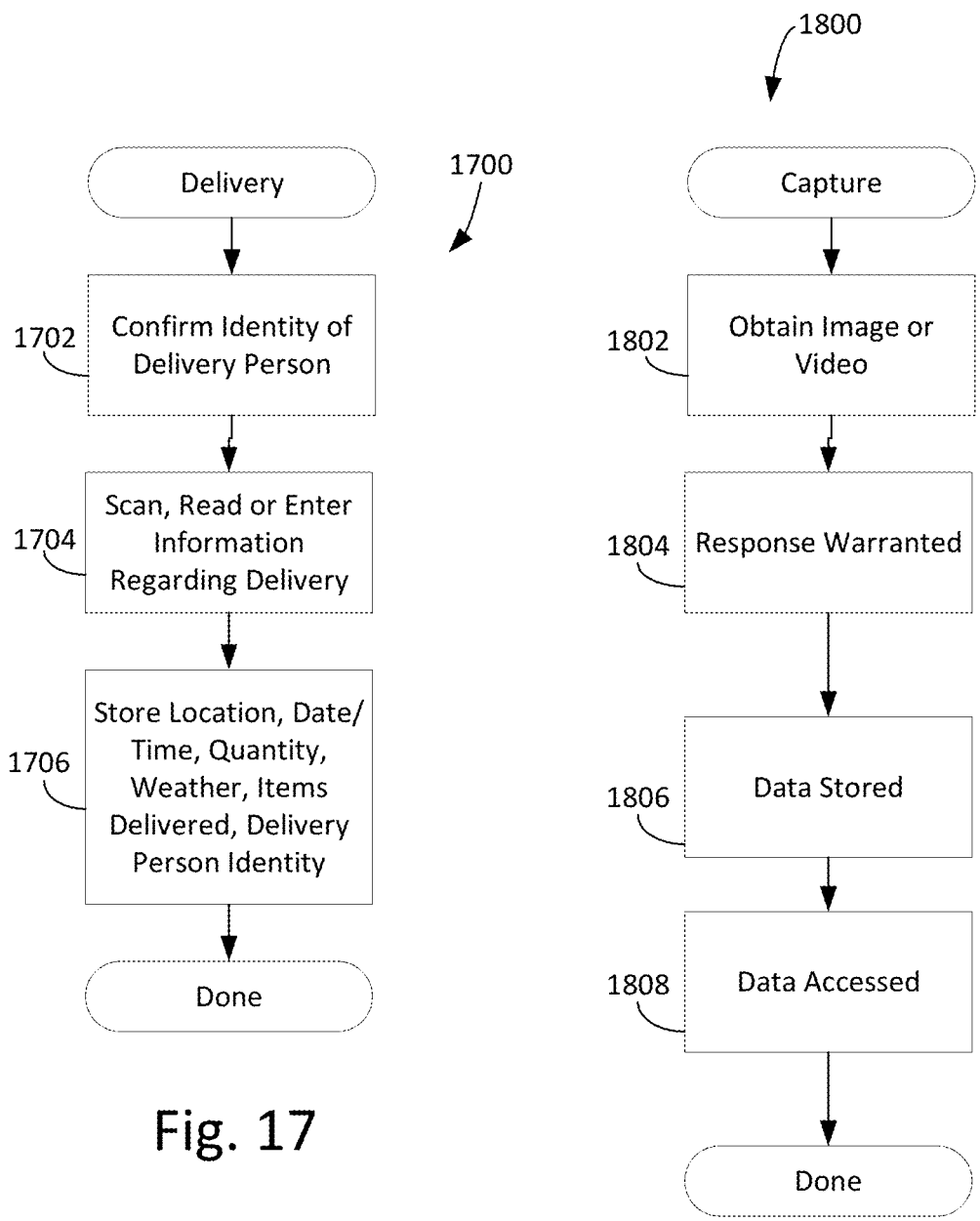

DECENTRALIZED SYSTEM FOR VERIFYING PARTICIPANTS TO AN ACTIVITY

RELATED APPLICATIONS

This application is a continuation-in-part from U.S. application Ser. No. 17/176,056 filed Feb. 15, 2021 which is a continuation in part of U.S. application Ser. No. 16/997,840 filed Aug. 19, 2020, which is a continuation in part of U.S. patent application Ser. No. 16/994,585 filed Aug. 15, 2020 entitled "System For Management Of Verification Of Project Commencement and Completion", which in turn is a continuation in part of U.S. patent application Ser. No. 16/991,916 entitled "System For Management Of Warranty Information For Projects And Materials", filed on Aug. 12, 2020 which in turn is a continuation in part of U.S. patent application Ser. No. 16/876,080 entitled "Digital Asset System For Management Of Projects And Materials", filed May 17, 2020 which in turn is a continuation in part of U.S. patent application Ser. No. 16/810,782, entitled "System For Management And Verification of Code Compliance", filed on Mar. 5, 2020 which in turn is a continuation in part of U.S. patent application Ser. No. 16/410,634, entitled "Use of A Persistent Storage Reference Construction Metadata and to Use Smart Contracts for a Project or process", filed on Jul. 12, 2019, U.S. patent application Ser. No. 16/510,642 entitled "Use of a Blockchain-Based Distributed Ledger and Smart Contracts for a Project or process", filed on Jul. 12, 2019 both of which are continuations of U.S. patent application Ser. No. 16/452,076, entitled "Site Super System For Project locations", filed Jun. 25, 2019 which all are incorporated reference.

BACKGROUND

1) Field of the System

A system for pairing a unique identifier associated with an individual with a digital representation, transaction or portion to creates a process for a verifiable link between the individual and such physical object, transaction or portion of a process.

2) Background

In the modern economy, there is a continuing trend for digitization. This trend includes attempts to create digital representations of individuals so that the individual can be digitally represented. Historical digitization focused on creating a digital representation of a physical object so that the digital information (e.g., representation) can be manipulated by information systems and stored on a database. It would be advantageous to create a digital audit of transactions or other occurrences associated with an individual for a series of transactions regardless of the physical location where the transaction occurs. One solution is to associate the physical object with a tag, label, or other items that have an identifier such as a code with alpha numeric characters such as a barcode with goods for sale, QR, RF ID and the like. While these prior attempts to pair physical objects with digital representations, these solutions are not complete. The UPC, for example, does not necessarily capture the changes to the part from year to year. This disadvantage is evidence when a replacement part is needed and while the UPC is the same, the actual part is not compatible with the good needing the part.

Attempts to use technology taken from industries such as the financial industry does not solve the problem as they cannot verifiably pair a digital representation with a physical object. Using the financial industry as an example, digitization begins with electronic information representing the dollar value of an account and not a specific physical dollar itself. As the financial industry progressed, the electronic current itself became the asset as discussed in U.S. Pat. No. 9,135,787, this patent discloses a Bitcoin kiosk/ATM that facilitates the buying or selling of Bitcoin. The underlying technology for Bitcoin is blockchain. Blockchain alone cannot verifiably pair a digital representation with a physical object because there is no linkage between the physical object and the digital asset under the Bitcoin scheme alone. Blockchain provides immutability, rather than the ability to pair physical objects with digital representation.

This type of digitization where the digital information represents the asset that is to be distinguished with electronic scanning of a physical assets. Electronic scanning simply creates a digital copy that is separate from the physical object and becomes an independent object itself. Despite the illegality of this example, the digital scan of US currency and the US currency itself are not equivalent. The US currency can be spent without reference or modification of the digital scan and the digital scan can be manipulated without reference or modifications to the US currency. The physical and the digital are not verifiably paired. The inability to pair the digital representation with physical object makes traditional digitization of physical objects challenging as the digital object and the virtual representation are not functional equivalents and therefore are not verifiably paired.

The ability to track object during a process can be improved when the object is properly and verifiable paired with a digital representation. In many industries, the systematic and logical workflow of physical objects increases the success of any project, process, activity, or providing a service. Generally, the creation or manufacturing of a good can include a designer that can specify materials, suppliers that can supply materials, that workers that may need a specific set of credentials, licenses or experience, and inspectors that can verify the delivery and performance of the goods and the manufacturing processes.

Currently, there is a lack of accountability, verification and reliability between physical objects and digital representations. The inability to verify the pairing of physical objects with digital representations negatively impacts current processes, increases risks, and increases costs in general. While there have been some attempts to add item information to a physical material, such as U.S. Pat. No. 8,321,302, these attempts have focused on tracking inventory levels and do not include verifiably pairing a physical object with a virtual representation. Further, these prior attempts focus on the identifier and not the physical object itself. Therefore, there is no assurance that the identifier remains associated with the physical object. This disadvantage can be seen in U.S. Pat. No. 8,521,620 which specifically states that if a RFID tag is lost or damaged, the system allows a user to enter an item number or style and tags of similar items are displayed, a new tag is generated and associated with the item having the lost or damaged tag. The ability to change RFID tags expressly shows that the physical object is not paired with the digital representation.

There have also been attempts to use inspection to assist with monitoring physical objects during a process. There have been attempts to provide for automated inspection such as U.S. Pat. No. 7,508,973 which discloses method of inspecting detects includes assigning a plurality of sets of image acquisition conditions, executing inspection using each of the sets of conditions, classifying all detected defects into real defects and false defects by use of an automatic defect classification function, and selecting, from the plurality of sets of conditions, a set of conditions ideal for detection. However, this attempt is reduced to a snapshot in time in the products lifecycle. This attempt does not pair the physical object to a digital representation, nor does it provide for an audit trail throughout the process.

There have been some attempts to improve tracking of articles such as shown in U.S. Pat. No. 7,898,403 that are directed to a method and system for detecting construction equipment process failures. A database is populated from information from a third-party source and a process failure report is provided for processes that are outside a norm assigned to the construction equipment asset. U.S. Pat. No. 7,031,930 is directed to a method and system for managing complex projects or processes by monitoring subcontractors in real time, against a system after commencement of the project. U.S. Pat. No. 8,004,397 is directed to a mountable reporting source comprising a controller coupled with an interrogating component configured for automatically receiving an identifier which is unique to an asset having a position determining component. U.S. Pat. No. 8,428,904 discloses product integrity tracking system, shipping label and associated method. This patent is directed to label body for attaching to a product to be shipped or to packaging containing the product.

These systems do not verifiably pair a physical object with a virtual representation during the life of a project or process and do not account for the physical goods being detached from the "tag". The inability to verify that a digital representation is paired with the physical object prevents the use of digital wallets since a digital wallet does not include such as pairing. Previous attempts to verify such transactions fail to pair a physical object with a digital representation, disadvantages that can be seen in United States Patent Application Publication 2019/0303919.

When the systems described above are However, using these prior methods for digital pairing a human individual with a digital representation is more problematic. These prior attempts go not create a transaction record, allow for decentralized verifications, provide for immutable and persistent storage and other limitations. For example, U.S. Pat. No. 8,650,103 discloses a system for verifying a person identifier and estimating whether it identifies the same person as another person identifier. To provide for the purported functionality, this system uses a verification system that communicates with online service providers. It is the online service provider that may hold transaction information so that there is no way to pair the individual with the digital representation including the digital representation of the transaction.

It would be an advantage to have a system that can verifiably pair an individual with a virtual representation of the activity, transactions, process of other information so that the information system can be used to immutable store such information and reduced or eliminated risks that the digital representations no longer represent the individual.

It would be advantageous to have a system that can provide for multi-party verification of the pairing.

It would be advantageous to have a system that can provide for tracking over multiple transactions, processes of other activity.

SUMMARY OF THE SYSTEM

In accordance with an exemplary embodiment, computerized system for A computerized system for verifiably pairing an in individual with a digital representation comprising: a computer system in communication with an immutable storage; a first data capture device in communications with the computer system; a second data capture device in communication with the computer system; a set of computer readable instructions included in the computer system configured for: creating a first event record from the first data capture device including, a first location, a first time and a first set of metadata wherein the first set of metadata includes a first digital representation of a first individual captured by the first data capture device, creating a subsequent event record from the second data capture device including a second location, a second time and a second set of metadata wherein the second set of metadata includes a subsequent digital representation captured by the second data capture device of a second individual, comparing the first set of metadata to the second set of metadata to determine if the first individual is the same as the second individual and, storing the first event record and the subsequent event record on the immutable storage.

The set of computer readable instructions can include instructions for receiving external data from an external data source associated with the first location and determining if the first location and the first event record is consistent. The external data can be taken from sources from the group consisting of public records, enterprise software, a local computer device and remote computer device and any combination thereof in communication with the computer system. The external data can be weather data and can include a position of the sun and the set of computer readable instructions can include instructions to determine if a shadow data is consistent between the weather data and the first set of metadata.

The first individual and the second individual can be the same individual and the set of computer readable instructions include instructions for retrieving the first event record and the subsequent event record, determining a timespan between the first time and the second time and determining if the same individual could travel between the first location and the second location within the timespan. The subsequent event record can include a verification data representing that a third individual retrieved the first digital representation of the first individual to verify that the first individual is physically present at the first location.

The computerized system can include a computer system in communication with an immutable storage; a set of computer readable instructions included in the computer system configured for: creating a first event record using a first data capture device wherein the first event record includes a first location, a first time and a first set of metadata wherein the first set of metadata includes a first digital representation of an individual, creating a subsequent event record using a second data capture device wherein the subsequent event record includes a second location, a second time and a second set of metadata wherein the second set of metadata includes a subsequent digital representation of a second individual; and, determining a timespan between the first time and the second time and determining if the timespan is consistent with the individual traveling from the first location to the second location.

The set of computer readable instructions can include instructions for determining if the first individual present at the first location is the same individual present at the second location. The first event record and the second event record can be stored on the immutable storage and are configured to provide an immutable audit record of time, location, and activity of the individual.

The first digital representation of the individual can include a unique biometric identifier which can be taken from the group consisting of facial recognition, an iris/retinal scan, a fingerprint scan, a hand scan, a voice print, or heart rate signature and any combination. The subsequent event record can include a verification data representing that a verifier viewed the first set of metadata and compared it with first digital representation of the first individual and the first individual to determine if the first set of metadata, the first digital representation of the individual and the individual are consistent. The first event record and the second event record can be stored on the immutable storage and are configured to provide an immutable audit record of time, location, and activity of the individual.

The system can include a computer system in communication with an immutable storage; a data capture device in communications with the computer system; a set of computer readable instructions included in the computer system configured for: creating an event record using the data capture device wherein the event record includes an event location, an event time and a set of event metadata wherein the set of event metadata includes an event digital representation of an individual, receiving external data from an external data source having external location data associated with the event location and determining if the external location data and the event location data is consistent.

The computerized system of claim 15 wherein the external data includes an external time, and the set of computer readable instructions include instructions for determining of the event time and the external time are consistent. The external data can be taken from sources from the group consisting of public records, enterprise software, a local computer device and remote computer device and any combination thereof and can include weather data. The weather data can include a position of the sun and determining if a shadow data included in the event metadata is consistent with the weather data.

The second event record can be stored on the immutable storage and operatively associated with the first event record and configured to provide an immutable audit record of the time and location of the first individual and the second individual.

BRIEF DESCRIPTION OF THE DRAWINGS

FIG. 17 is a flowchart of aspects of the invention;
FIG. 18 is a flowchart of aspects of the invention.

DETAILED DESCRIPTION

The present system provides for verified pairing of an individual with a virtual representation including virtual representations of one or more transactions, processes, or other activities.

Figure 1A:
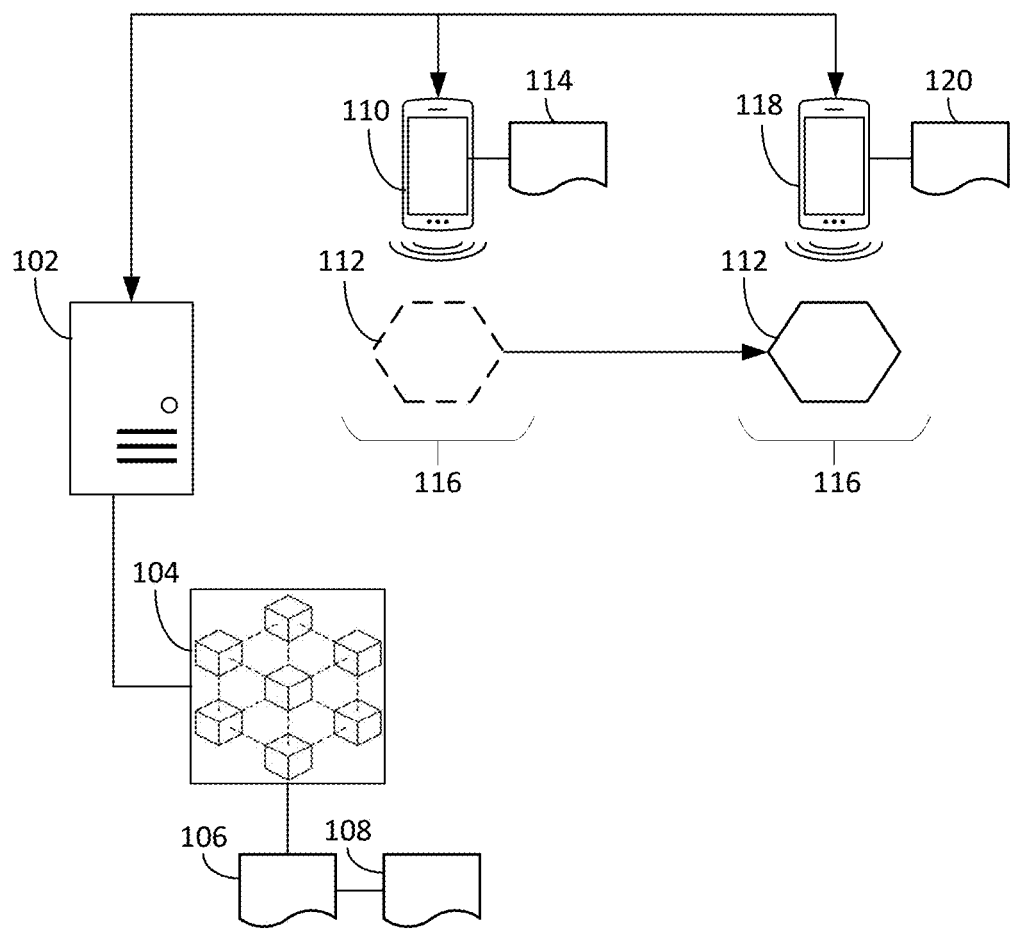
FIG. 1A is a diagram of aspects of the invention.

Referring to FIG. 1A illustrates a computer system 102 can be in communications with a data storage system 104. The data storage system can be permanent, immutable, and persistent so that the information stored on the data system, once storage, cannot be changed. The data system can include a plurality of computer systems where data can have copies onto each computer system. When using the data storage system, the data can be static so that once created and stored, it cannot be changed. Examples of data storage platforms include hard drives, solid state drives, tapes, and cloud storage systems. The immutable data storage system can use blockchain, crypto-shredding, WORM, append only, distributed ledger technology, immutable cloud storage, immutable record retention such as Oracle Cloud Infrastructure Object Storage, and any combination thereof. In one embodiment, the immutability is accomplished by the data storage system only allowing records to be appended to the storage media without the ability to modify the record one written. One such system includes blockchain. When a first record 106 is written to the data storage system, the record cannot be changed. When a second record 108 is written to the data storage system, it is stored later in time to the first record thereby effectively providing a chronologically trail of events associated with the individual and the digital representation of the individual and activity. In one embodiment, the second record can include information linking it to the first record including a hash from the first record.

In one embodiment, the first record can be associated with a first event and a second record can be associated with a second event. Each record can include biometric data of an individual associated with each event. The individual can be the same individual for each event of difference individuals for each event. These events can be transactions, processes, or other activities. The order the first record and the second record can be written on the immutable storage can be used to show that some period of time elapsed between the first record and the second record. This functionality can add to the verification process and attempts to improperly tamper with the immutable storage may be discovered when the first record and the second record are not in chronological order. Further attempts to improperly tamper with the immutable storage can be discovered when the metadata of the first record and the second record are inconsistent with the first record and the second record being stored chronologically. For examples of the metadata of the first event includes a first time and first location and the meta data of the second event include a second time and second location where it is physically impossible for the individual associated with the two events to physically move between the first location and the second location in the time between the first time and the second time.

The first event record can be associated with a first event and the second event record can be associated with a second event. The data associated with these events can be retrieved from a capture device and used in creating and writing the associated event record. The data captured can include biometric data of an individual associated with one or more events. If the date and time setting of the data capture device are incorrect, this discrepancy can be identified by comparison with the event record created and compared to related records in the immutable storage. In one embodiment, metadata integrity used by the system can be designed to identify inconsistencies with date and time. The first event can differ from the second event by time, activity, process, location, or any combination.

In one embodiment, metadata associated with the event and event record and a ledger hash time, representing when the event record is stored (e.g., committed) to the immutable storage can be used to validate the metadata provided from the data capture device. If the data capture device has an incorrect time, a comparison of the ledger hash time with the metadata from the data capture device can identify an error. Identifying an error can be used to alert users to data capture device issues and can indicate that the data capture device needs to be serviced or replaced prior to its next use. The data capture device can include a biometric reader or scanner. The metadata captured from the data capture device can include the device identification, model, manufacturer information, error codes, status information, user data, environmental data (e.g., weather data), software information, hardware information, date field information, and the like.

The metadata can include biometric data that may include facial recognition, an iris/retinal scan, a fingerprint scan, a hand scan, a voice print, or heart rate signature and any combination. The metadata that can be associated with the capture device can include weather conditions, which can include a sun angle, which can be compared with environmental weather conditions to approximate the data capture time. Metadata associated with an image or video can be used to verify weather conditions in the image or video. Metadata associated with an image or video can be used to verify biometric data of the individual.

For example, a camera can capture an image of an individual. The metadata (e.g., a first metadata) associated with this image can include the date, time, locations, device number and other data. The image can include in the background the shadow of the individual or a shadow of another object. Weather information (e.g., a second metadata) can be accessed from a third-party source such as the national weather center or standard organization such as the National Institute of Standards and Technology and the National Oceanic and Atmospheric Administration of the United States Department of Commerce. One verification can include that the image shows that at the captured locations, date and time, there was sunlight. The weather data can indicate if it was sunny. If these two conditions exist, the confidence that the individual was at the captured location and the date and time that the individual was at that location is increased and included in the verification.

The system can also retrieve the previous capture location, date and time (e.g., a third metadata) of the individual and compare it to the currently captured location date and time. A determination can be made concerning the time and speed it would take to travel from the previous location to the current location. For example, the previous location is 30 miles from the current location and the time difference between the previous data capture and the current data capture is 10 minutes, confidence that the current data capture is accurate is reduced.

For example, the video can use facial recognition to verify that the individual entering a fingerprint is the same individual recognized on the image. Time and location metadata can be retrieved from publicly sources or remote sources and captured with the device metadata to determine of the captured weather in the image or video is the same as being reported locally on that day and at that time.

The metadata that is captured can be dependent upon the device and can include metadata associated with an individual (e.g., worker), equipment, weather, enterprise software, security hardware and software, material, indicia, smart contracts, public records, authentication information, date, time, location, entity and any combination of these examples.

In one embodiment, an image or video captured can be used to identify an approximate time where data, including biometric data, was captured by the data capture device. The metadata associated with the data capture can include weather conditions, sun angle, which can be compared with environmental weather conditions to approximate the data capture time. In one embodiment, the data capture can include the location so that the location of the data capture device can be used to retrieve environmental weather conditions when the data capture occurs. In one embodiment, the system can determine the length of a shadow and according to the position of the capture device, the time of day can be determined. Using this information, the confidence of the accuracy of the time of the capture device can be increased. This information can also be used to increase the confidence in the accurate of the capture device reported location as the shadow length should be consistent with the location, object height and time.

The data capture device can capture data in response to an event associated with the physical object. For example, if the physical object's location changes, is modified, transferred, integrated, or other action, process or procedure associated with the physical object can signify an event. A location can include a manufacturing place, construction site, business providing services (e.g., vehicle repair service), origination site, delivery site or other location where the materials will be used including the creation, maintenance, repair or integration into an assembly. Further, if an individual interacting or otherwise associated with a physical object changes, such data can be captured.

Verification, including verification of an event, can include verifying that the individual information and the virtual representation match and can be accomplished in a variation of methods including capturing biometric information, capturing a image of video, capturing indicia such as a card, fob, of other item otherwise associated with the individual. The identification of an individual performing or otherwise associated with an event can be captured by identification devices (e.g., cards, tags, RF ID) and biometrics including visual capture (e.g., facial recognition), voice recognition, iris scan, fingerprint, palm print, weight, dimensions, change in weight, dimensions or other attributes, and any combination. Examples of verification processes can include having stored data about the physical object and comparing the physical object with the date, using machine learning process video, using imagery, audio clips and other media to and any combination. Individuals, such as inspectors or verifiers, can be used to verify physical objects and events onsite and offsite. Individuals can process video, imagery, audio clips and other media to verify assets and events and provide the verification to the system at one or more events. Upon verification of an event, smart contracts can be executed according to verification of the physical object and event. The individual preforming these activities can be identified through the capture of biometric data. The system can also retrieve event records that can include data and metadata about an individual, including biometric data. The data and metadata from a first record can be compared with a second record or subsequent record to determine if the individual represented by the first record is the same as the individual represented by the second or subsequent record.

In operation, a first data capture device 110 can be in communications with the computer system 102 so that data captured by the first data capture device can be transmitted to the computer system. The first data capture device can have a first capture device metadata 114 originating from the data device that can be included in the first record 106. Capture device metadata can include the biometric data of the individual associated with an event. The first data capture device can capture data associated with the physical object and the individual. Object data can include an image of the physical object or individual, tag, label, RFID, weight, dimensions, and other indicia and any combination thereof. The object and individual data can be captured at a first event 116 that can include a change in state of the physical object, change in location change in time or any combination thereof. When an event occurs, which can be a second event, a second data capture device 118 can have a second capture device metadata 120 originating from the data device that can be included in the second record 108. The second data capture device can also capture object and individual data associated with the physical object and individual 112 at the second event 120.

During data capture by the first data capture device, indicia can be capture where the indicia is associated with the object or individual. The indicia can include biometric data, an image, a label affixed to the object, a radio frequency identification (RFID) tag, an ultra-high frequency (UHF) tag, a bar code, a QR code, a Bluetooth beacons, alpha-numeric characters, and any combination thereof. The indicia can be included in the first event record and stored on the immutable storage. When a change in time, location or other event occurs the second data capture device can capture the indicia. Once captured, the indicia can be compared to the indicia in the first event record and if the two matches, then verification exists that the individual associated with the second event is the same individual that was present at the first event. In one embodiment, the second capture device can capture data, transmit the data to the computer system 102 and computer readable instructions on the computer system can perform the comparison of the indicia capture as the second event with the indicia included in the first event record.

Figure 1B:
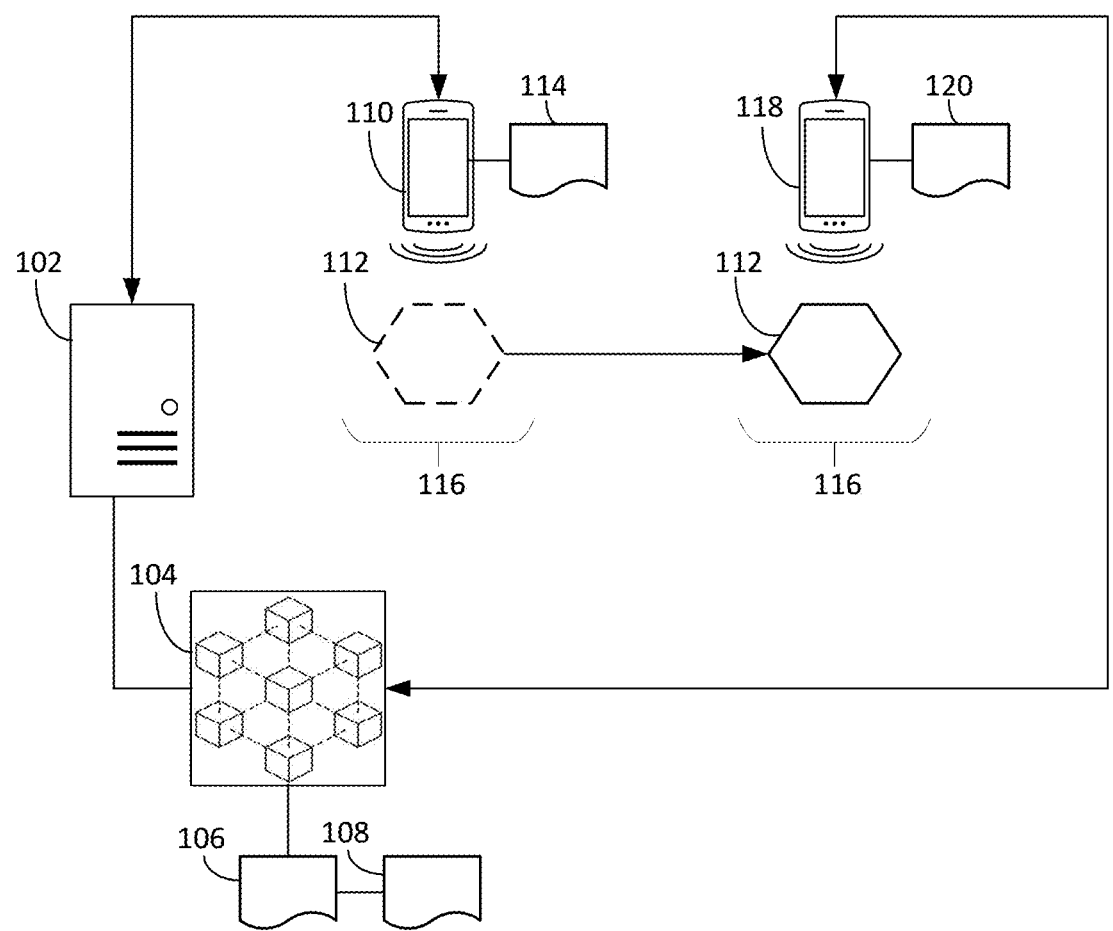
FIG. 1B is a diagram of aspects of the invention.

Referring to FIG. 1B, the second data capture device can be in communications with the immutable storage. Computer readable instructions on the second data capture device can capture the data at the second event, retrieve the first event record, compare the indicia from the second capture device with the indicia of the first event record and determine if the physical at the second event is the same physical object at the first event. In one embodiment, the second data capture device can store a second event record that can include indicia capture at the second event on the immutable storage. The computer system can be notified that a second event record has been stored. The computer system can retrieve the first event record and the second event record and compare the respective object indica to determine of the physical object is the same physical object at the first event and the second event. If the object indicium is not the same, a notification can be provided indicating that the physical object has been changed, modified or otherwise different between the first event and the second event.

Figure 1C:
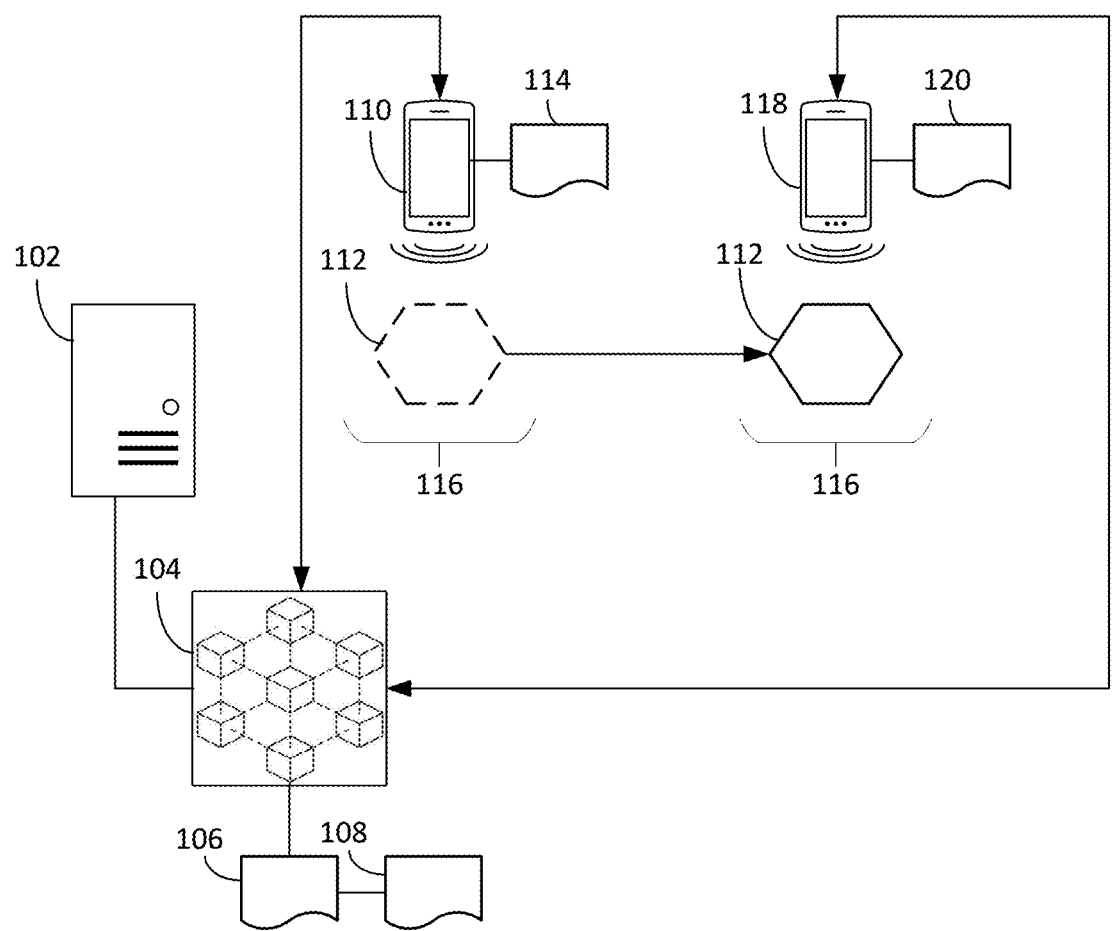
FIG. 1C is a diagram of aspects of the invention.

Referring to FIG. 1C, the first data capture device can be in communication with the immutable storage. In one embodiment, the first data capture device can capture data at a first event that can include indicia, create a first event record, and store the first event record on the immutable storage. The second data capture device can retrieve the first record having the indicia from the immutable storage and compare the indicia captured by the second data capture device with the indicia of the retrieved first event record. The first data capture device and the second data capture device can be the same device.

The system can therefore pair an individual with a digital representation, such as an indicium, and verify among events that the individual has not changed. The system can also determine if the biometric data of the individual capture during an activity is the same data or represents the same individual in the previous of subsequent record. The system can also determine if the biometric data of the individual capture during an activity is the same different data or represents a different individual from the previous or subsequent record.

Referring to FIGS. 1A to 1C, the data capture devices can serve as data capture nodes for a system where the data capture devices are distributed. The data and metadata that is capture from the data capture devices can be transmitted directly or indirectly to the immutable storage. The stored data and metadata can be configured to provide for an immutable digital audit trail wherein each metadata stored can include time, location, and activity of the individual and physical objects. When needed, the stored data and metadata can be accessed and using the time, location, activity, individual or physical object, linked together to form the immutable digital audit trail. Multiple audit trails can be provided according to time, location, activity, individual, physical object and any combination. For example, if there is an inquire as to the status of a delivery, the system access the data and metadata and retrieve the data and metadata associated with a physical object, arrange the data and metadata in coprological order, and determine the time and location that the physical object was present to assist with tracking the physical object and the individual associated with the physical object (e.g., delivery worker, assembler, retail seller and the like).

In one embodiment, a first data capture device can be in communications with a second data capture device so that the data and metadata from the first data capture device can be compared to the data and metadata of the second data capture device to provide a level of verification of the data and metadata captured by each device. For example, if the first data capture device and the second data capture device both capture the same individual biometric data within a predetermined period of time and the distance between the first data capture device and the second data capture device can be traveled in the predeterminer period of time, the confidence that the individual was at both locations at the time indicated is increased. Further, the first data capture device can be a kiosk and can be in communication with the second data capture device.

Figure 2:
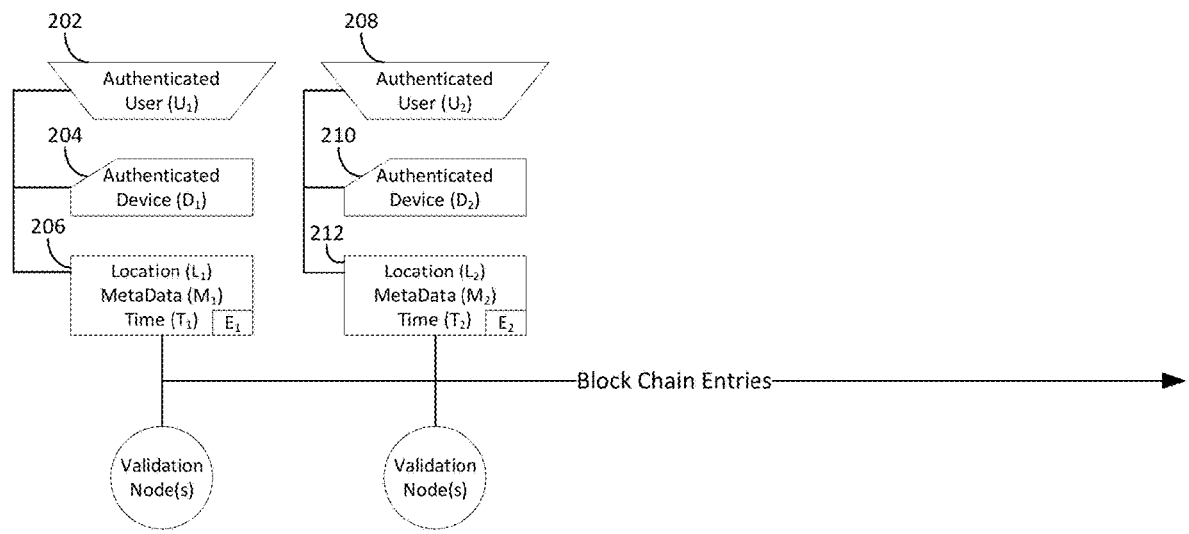
FIG. 2 is a diagram of aspects of the invention.

Referring to FIG. 2, one embodiment the user or individual of a data capture device can be verified at 202 so that the user can be authorized to use the data capture device or to perform data capture at the first event. The data capture device can be authenticated at 204 representing the data capture device is the correct data capture device and is in working order. The metadata that can be captured by the data capture device can include a location, a time and additional metadata shown as 206. The user can be a first user and in one embodiment a second user of a data capture device can be verified at 208 so that the user can be authorized to use the data capture device or to perform data capture at the first event. A second data capture device can be authenticated at 210 representing the data capture device is the correct data capture device and is in working order. The metadata that can be captured by the data capture device can include a location, a time and additional metadata shown as 212. In one embodiment, the first event record and the second event record can be committed to immutable storage such as blockchain using validation nodes included in the immutable storage structure.

Figure 3:
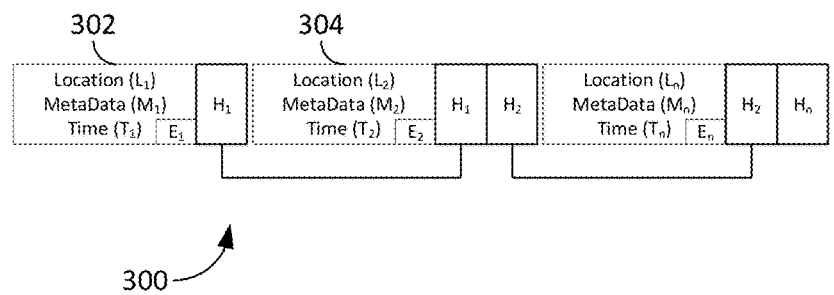
FIG. 3 is a diagram of aspects of the invention.

Referring to FIG. 3, in one embodiment the second event record 44 can be linked to the first event record 302 to create a digital audit trail 300 that includes indicia verifying that the individual remains the same or has changed. The digital audit trail can include the individual(s) that are associated with each event in the audit trail. The digital audit trail can also be used to determine if the physical object remains the same or has changed throughout the process transaction or other activity. The digital audit trail can also determine if when during the timeline of the transaction, process of other activity the individual or physical object changes.

One example of the invention can include when a material is selected for transport by the supplier, a shipping company can be sent a shipping order representing the material to be transported, an origin and a destination. The shipping order can be provided directly to the shipping company or can be retrieved from the immutable storage. Once the shipping company receives the shipping order, a driver can travel to the origin and receive the material which can represent a first event, and capture data associated with the first event. The driver can be identified and associated with the first event. A first event record can be created representing that the driver and therefore the shipping company received the materials and pair the received material with indicia, the driver with the indicia and the driver with the receipt. In one embodiment, verification that the material is associated with the indicia can be performed by an individual receiving the material. In one embodiment, verification that the driver associated with the shipment can be performed by a second individual.

Once that material is delivered to the destination, the driver can unload the material, a second event, a second verification can occur verify that the driver was the individual that delivered the materials to the destination and that it was the same driver that received the material at the origin. A second event record can be created representing that the material was delivered and that the material matches the material at the origin and described on the shipping order and that the same driver preformed these tasks. The second event record can include the environmental conditions when the material was delivered, delivery notes and the like. The destination can be a receiving entity that can create a third event record representing that the material ordered was received. A receiving individual can be identified and associated with the activity. The receiving entity can use a third data capture device to capture the indicia and create a third event record that can be associated with the one or more individuals in the activity. The computer system second data capture device and third capture device can verify that the delivered material matches the ordered material, the driver and receiver involved, and that the material has not been modified, changed, substituted, or otherwise different from the origin to the destination.

The receiving entity can use a data capture device that can include biometrics or other indicia to verify that individuals handling the material are authorized and have the necessary licenses, work certifications, experience, authorizations and other requirements as well as assist with payroll and insurance verification and coverage.

In one embodiment, the computing logic may allow authorized individuals to manually enter the presence of another authorized individual, including on the controller at the project location or through a remote device that can be determined to be at the project location, within a boundary associated with the project location, in proximity to the system. In one embodiment, individuals may be verified and paired with a virtual representation using two-factor authentication. The individual can be identified using biometrics that can be included in the record that can be stored in the immutable storage.

The receiving entity or individual can be uniquely associated with a location. A location marker can be affixed at the receiving entity and uniquely identify the receiving entity and in one embodiment, a project location. The location marker can be read by a data capture device and provided to the computer system and the immutable storage. In one embodiment, the receiving entity can receive metadata such as individual information, a shipping identifier associated with the delivery, including a truck, trailer, pallet, or other container so that the materials are known to be received at the project location.

The computer system can be contained in a housing such as a kiosk and can be physically associated with a project location. The project location can be defined by a boundary representing the perimeter of the physical location. The system can include a sensor and reader which can be selected from the group consisting of radio frequency identification (RFID) detector, ultra-high frequency (UHF) detector, a bar code scanner, a QR code scanner, near frequency communication (NFC) device; Bluetooth beacons, an optical character recognition (OCR) device and any combination thereof. An environmental sensor, such as a weather sensor or weather station, can be in communications with the or included in the housing and configured to record the weather and other environmental conditions at the location and at different times during the project. If the environmental sensor detects a change in the environmental condition, it can represent an event.

The system may record the date and time of events such as the arrival and departure of materials, individuals, workers, supplies, third parties, inspections, and the like to and from the project location, the date and time associated with environmental conditions including weather. The environmental conditions can be used to modify the schedule for workers so that workers are not working during inclement weather, tasks are not preformed outside specified environmental conditions, and materials are delivered and installed during specified environmental conditions.

The system may track the movement of material at a project location or during a process or to and from the project location thereby creating an audit trail associated with the individual and material. Scanning technology such as RFID readers, UHF readers and/or the like may be utilized to assist the location tracking for tools, equipment, materials, and individuals. The tracking the individuals assists with reducing the risk of loss, theft, mis-delivery, and the like. For example, the tracking solution may indicate instances of possible theft, such as when the materials are leaving the project location when the removal of the materials is not proper. The system can determine the individual that preforms unauthorized activity through biometric data.

The system may allow for the establishment of one or more geofenced zone that can be associated with delivery areas, individual entrance exit areas, task areas, storage areas, assembly areas, distribution areas and any combination thereof. These areas could be monitored and established with access allowances or restrictions to control movement of material, individuals, and equipment to assist with the prevention of loss, mistakes, inefficiencies, and damage. The system can assist with verification that individuals entering or exiting an area are consistent with authorization levels for that area, the material in the area of the individuals. A first event can be a first individual handling the material at a location in a first zone and a second event can be the individual depositing the material in a second zone. The first event can be associated with the first zone and a second event can be associated with the same zone, but at a later time.

The system can also use smart contracts associated with events and stored on the immutable storage that can be self-executing upon satisfaction and verification of contractual terms and objects associated with an event. For example, when an individual performs a certain transaction, process or other activity, a smart contact that instigates payment to the shipper can be performed.

Figure 4B:
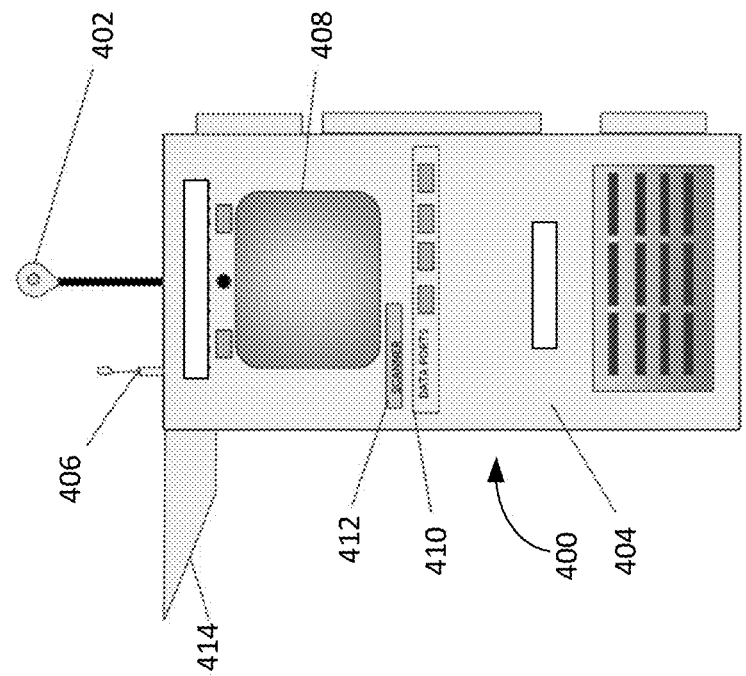
FIG. 4B is a schematic of aspects of the invention.
Figure 4A:
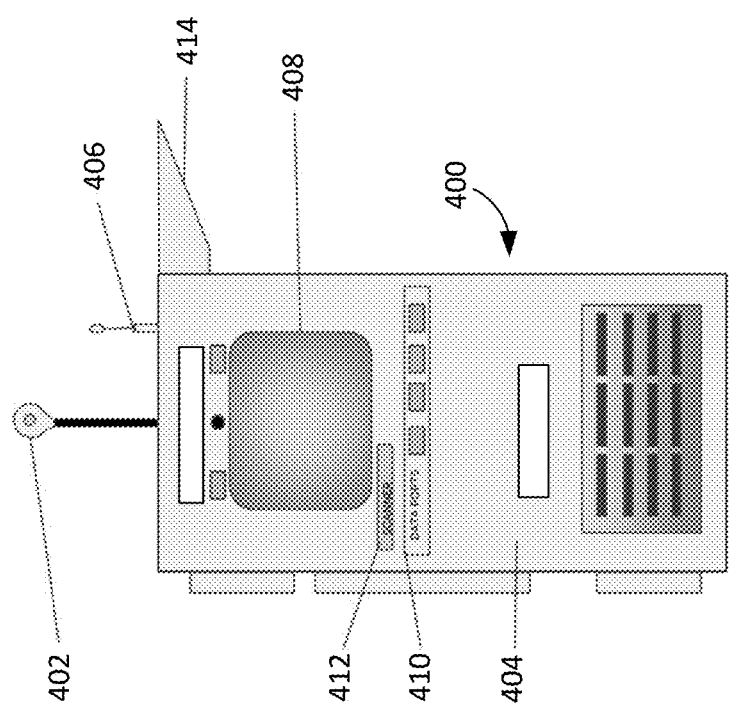
FIG. 4A is a schematic of aspects of the invention.

Referring to FIG. 4A, in one embodiment the computer system can be contained in a housing 404 can be physically associated with the project location, virtually associated with the project location or both. A unique location marker can be disposed at the project location to uniquely identify the project location. For examples, a transmitter such as a RFID can be associated with the project location by embedding it is a permanent fixture such as a concrete slab, foundation, structure, and the like. The system can read the information from the location marker and associate its actual location with the project location. The location marker can include an alpha, numeric, or graphical information such as a number, letters, barcodes, QR code, physical or geographic coordinates (e.g., GPS coordinates), passive transmitter, active transmitter and the like. Each system can have a unique identifier and each project location can have a unique identifier.

A first side of the system 400 can include a camera 402 for obtaining information about an individual, images of materials, equipment, individuals, or other items entering or leaving the project location as well as images of individuals along a perimeter. The camera 402 may capture biometric images upon which biometric recognition may be performed. Multiple cameras may be placed on or around the housing. The cameras may have biometric recognition and motion detection capabilities. System 400 may include an addition to the camera 402 or instead of the camera 402, biometric-based identification devices that may be used to confirm the identity of individuals entering, leaving or on the perimeter of the project location. The system 400 may include an antenna 406 for communicating with a network including a wireless network, Wi-Fi network, Bluetooth, quantum networks, cellular network (e.g., 4G or 5G network) and any combination. The system 400 may include a housing 404 made of suitable weather resistant material, appropriately sealed to protect the internal hardware. The system 400 may include a display 408, such as a touchscreen display, upon which information may be displayed and entered. The display 408 may include an integrated camera that may be used to capture images and that may be used in performing facial recognition of individuals. The display may also include or operatively associate with one or more integrated speakers for providing audio output, a microphone for receiving audio information to facilitate two-way communications to a remote location. The system 400 may include a scanner 412 for scanning items including biometric data and information associated with materials, transactions, processes, and other activities. as explained below. The scanner 412 may be, for example, a QR scanner, an Optical Character Recognition (OCR) or a bar code scanner 412 in some instances. The side of the system 400 shown in FIG. 4A can be used for deliveries and inspections. A individual such as a delivery person may scan delivered materials, equipment, or other items via the scanner 412 and may interface with the system using the touch screen display 408. An individual such as an inspector may scan or take images of inspection documents via the scanner 412 or camera and may interface with the system using the touch screen display 408. In some embodiments, there may be fewer sides in which to interact with the system for all authorized personnel. An overhang 414 may be provided to assist in decreasing glare and protecting some of the items on the housing from the weather.

FIG. 4B depicts a side of the system 400. This side can include a touch screen display 408 as well as a scanner 412. Display 408 may include or be operatively associated with an integrated camera for capturing images, speakers for providing audio output and a microphone to facilitate two-way communications with a remote location. Still further, this side of the system 100 may include data ports 410. The system 400 may be accessed to gain access to equipment, tools and to sign in or sign out when leaving or entering the project location, as will be described below.

Figure 4C:
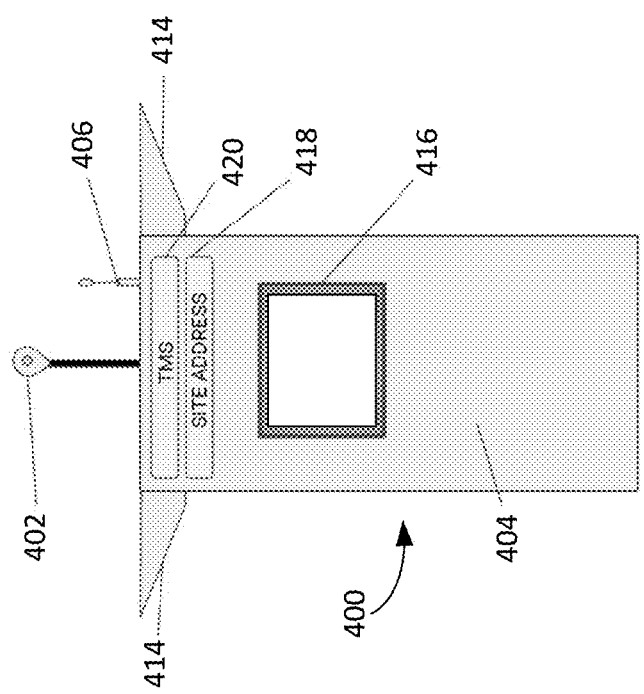
FIG. 4C is a schematic of aspects of the invention.

FIG. 4C shows a third side of the system 400. This side has a location 416 in which information such as permits, specifications, instructions, tax information, plans, and the like and may be displayed. In some embodiments, the information displayed may assume electronic form so that a video display is provided in the area 416 of the housing 404. A tax map submap (TMS) number 420 for the project location may be displayed on the housing 404. Other location identifying information can be displayed such as location number, store number, assembly number, area within the project location and the like. In addition, the site address 418 may be displayed on the system 400. The site address may refer to both the mailing address for the project location and/or other physically identifying information associated with the location.

Figure 6:
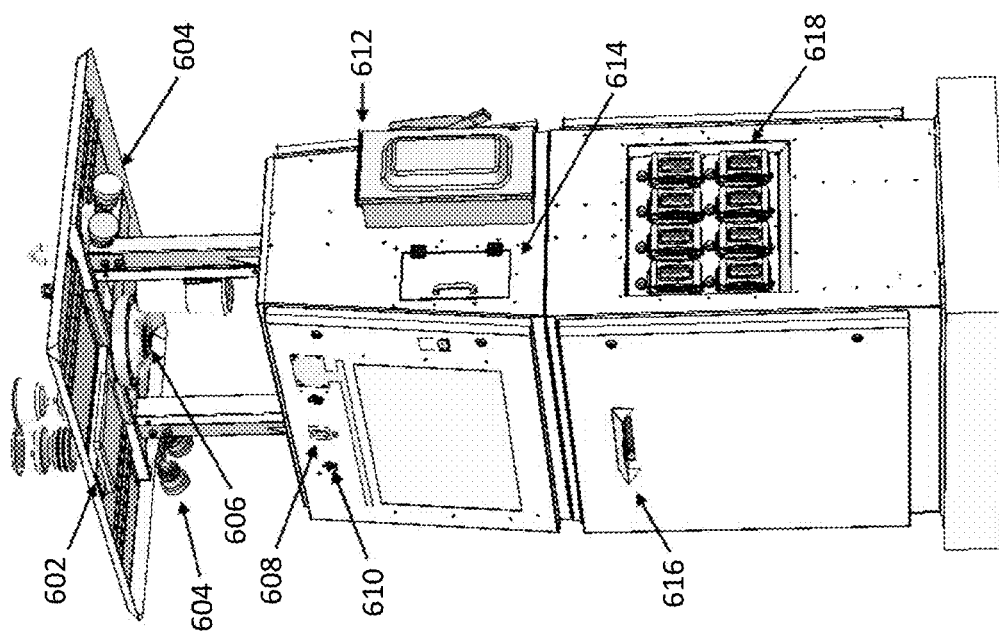
FIG. 6 is a schematic of aspects of the invention.
Figure 5:
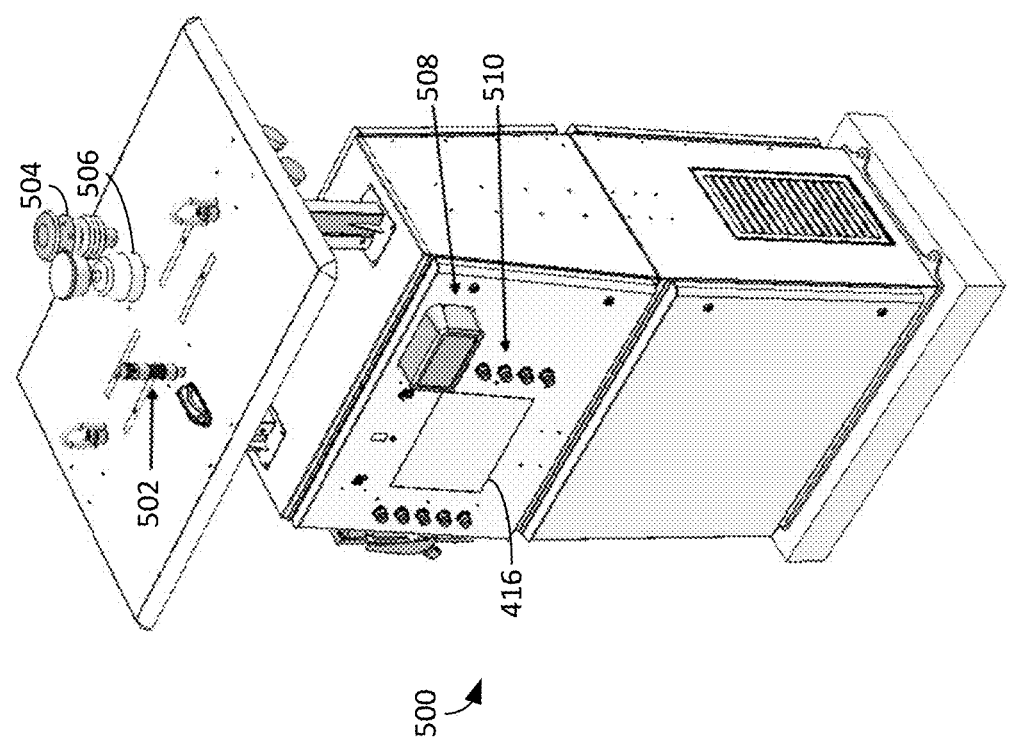
FIG. 5 is a schematic of aspects of the invention.

Referring to FIGS. 5 and 6, the housing 500 can include an individual (e.g., human) side that is configured to be used by an individual at the project location. The housing can include an alarm indicator 502 that can be actuated as described herein. The housing can include a weather station 504 that can include an integrated or separate fluid (e.g., rain) collector 506. Biometric reader 508 can be included. Display 416 can be proximity to input assemblies such as buttons 510. The housing can include a field receiver 602, lights 604 and camera 606. One or more cameras can provide a 360° field of view and include a wireless connection for transmitting images to a remote computer device. The images captured can be used for biometric identification of individuals. The images can also be used for input to the system including input allowing the system to identify delivered materials. The system can include one or more second cameras 608 such as webcams disposed at various locations around the system for capturing images. The lights can include motion activation and photoelectric activation. Speakers 610 can be included to provide audio information to an individual, user, worker, inspector, or other party using or near the system. The audio information can include instructions, alarms, and the like. Power junction 612 can include a shut off switch that can be used in emergency and non-emergency situations. The system can include a secondary power source, such as a battery, so that when the main power is shut off, an alarm can sound, notification send to a remote computer device of other indication that the system or power source has been powered down. The system can include a hand scanner (not shown) that can be protected by a hand scanner access door 614. A document scanner 616 can be included in the system for receiving physical documents, converting the physical document into a digital representation, and storing the digital representation on the computer readable medium or the immutable storage. The system or housing can include electrical outlets 618 for providing power to various tools and equipment at the project location including recharging batteries. The system can include a wired connection to remote computer devices of a transceiver to provide a wireless connection to remote computer devices.

Figure 7:
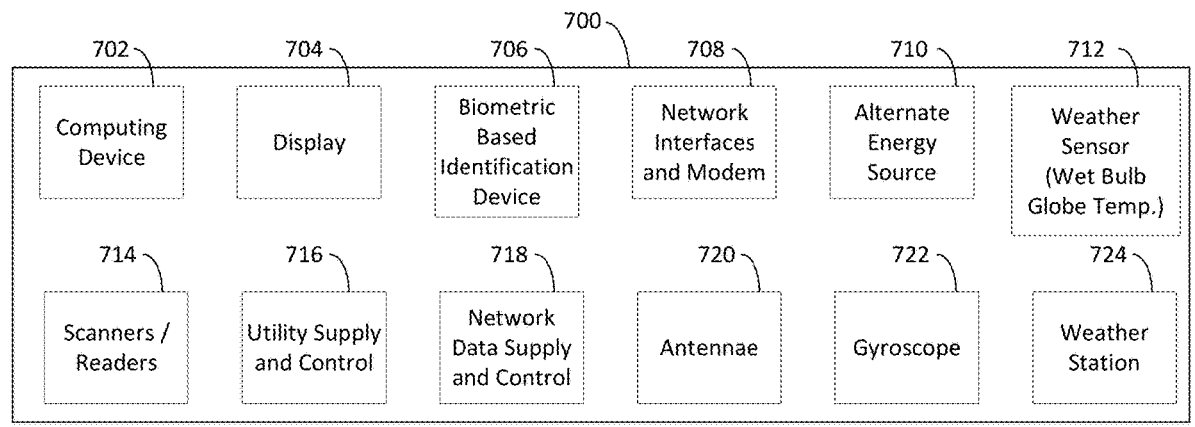
FIG. 7 is a schematic of aspects of the invention.

FIG. 7 depicts components that may be included in the system of exemplary embodiments even when not included in a housing. The system may include a computing device 702. The computing device 702 may take many different forms indicating a desktop computing device, a laptop computing device, a mobile computing device, an embedded system, a smartphone, special computer device, custom computer device, or the like. A display 704 may be integrated with the computing device 702 or as a separate device, such as a liquid crystal display (LCD) device, a light emitting diode (LED) display device or other types of display devices on which computer information may be displayed. One or more biometric-based identification devices 706 may be provided. As will be explained in more detail below, multiple biometric-based identification devices may be used. Network interfaces and a modem 708 may be provided. The network interfaces may interface the computing device 702 with a local area network or a wide area network wherein the networks may be wired or wireless. A modem may be provided to communicate telephonically or over cable lines with remote computing devices.

The system 700 may include various scanners and readers 714, such as those described above relative to housing. The system 700 may include a utility supply and control 716 and a mechanism for turning the utilities, such as power, gas and/or water, on and off under a programmatic control. The system 700 may include an internet data supply control 718 and a mechanism for turning the access to this service on and off under a programmatic control. Programmatic control may be provided to grant or deny access to such resources. The system 700 may include an antenna 720 for wireless communications signals to receive and transmit. The system 700 may include a gyroscope 722 to monitor any moving of the system. The gyroscope 722 may indicate motion indicative of whether someone is trying to move or tilt the housing or other component of the system. Logic may be provided to send a notification in such an event where the gyroscope indicates substantial enough movement. The gyroscope or accelerometer can be used to detect motion corresponding to input from an individual by detecting the motion that can be associated with pressing a button of screen, entering data, reading a finger por palm print, positioning a device for a rental or face scan and the like. The detected motion can be associated with the data and metadata and assist with verification that an individual interacted with the data capture device and is in close proximity to the data capture device.

The system 700 may include a weather station 724 to measure current weather conditions, such as temperature, air movement, humidity, precipitation, barometric pressure, direct sunlight, and the like. Input from the weather station 724 may be used to inform decision making by the system in some instances. Alternatively, the weather may be collected via software, such as from a weather service or other weather source. Similarly, the system 700 may include a weather sensor 712. The sensor can be a wet bulb globe temperature adapted to measure, among other things, heat stress in direct sunlight, which accounts for temperature, humidity, air movement (direction and speed), sun angle and cloud cover (solar radiation).

Figure 8:
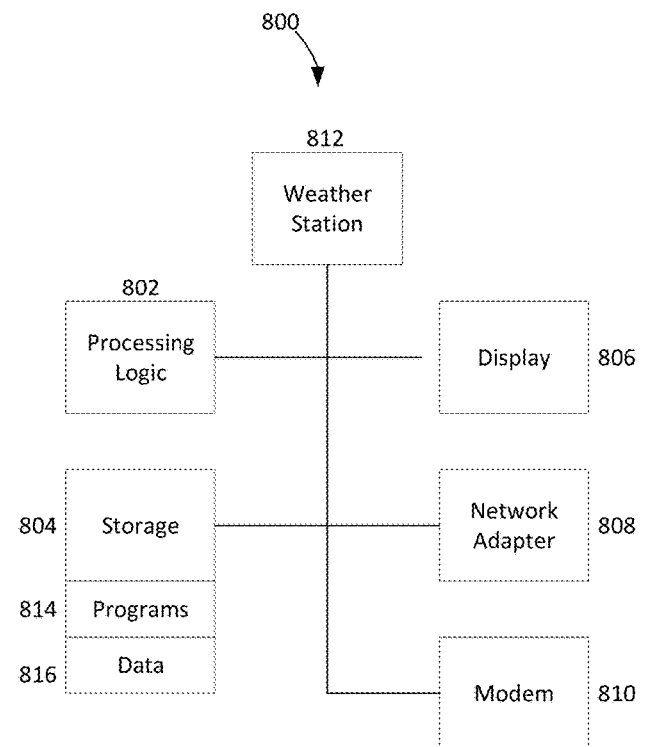
FIG. 8 is a schematic of aspects of the invention.

FIG. 8 shows an example of a computing device 800 for the system. The computing system may include processing logic 802, such as microprocessors, controllers, field programmable gate arrays (FPGA), application specific integrated circuits (ASICs) electronic circuitry, and other types of logic. The processing logic 800 performs the operations of the computing device 802. A local storage device 804 may also be provided. The computer readable medium and/or data storage device 804 may take various forms, including magnetic storage, optical storage, etc. Storage capability 804 may include computer-readable media, including removable computer readable media, such as disks, thumb drives and the like, or disk drives, solid state memory, random access memory (RAM), read only memory (ROM) and other types of storage. The computing device may include a display 806, such as an LCD display, an LED display, or other types of display devices on which video information may be displayed. The computing device 800 may include a network adapter 808 for interfacing with networks and a modem 810 for communicating wirelessly, over telephone lines or cable lines with remote devices. The processing logic 802 may use information stored in the storage device 804. In particular, the processing logic 802 may execute programs 814 stored in the storage and may access and store data 216 relative to the storage device 804. The computational functionality of the system described herein may be realized by the processing logic 802 executing the programs 814.

Figure 9:
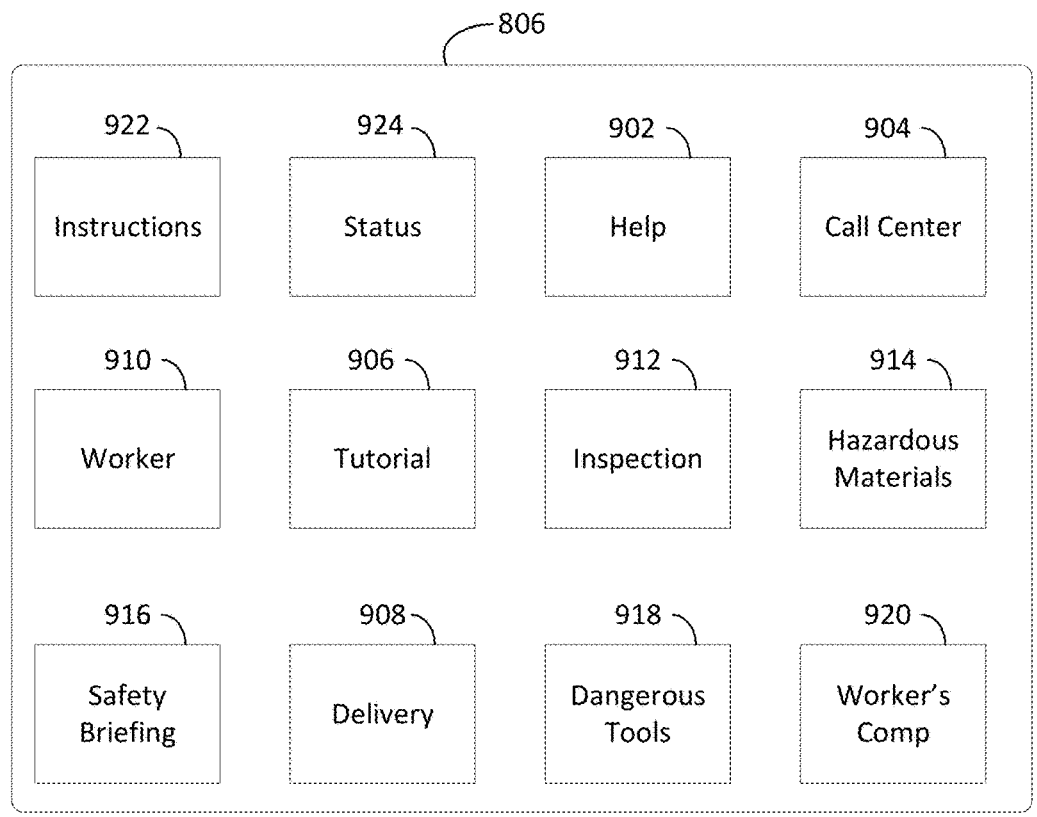
FIG. 9 is a schematic of aspects of the invention.
Figure 10:
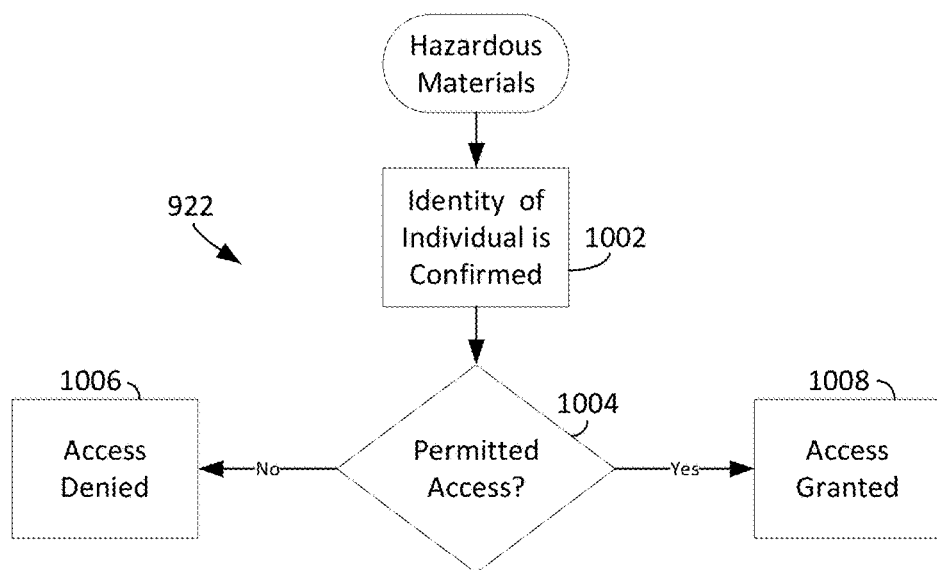
FIG. 10 is a flowchart of aspects of the invention.

FIG. 9 shows an example of a user interface on display 806, such as found in the housing 400 In Figure. The user interface may include activatable elements. A user may depress these activatable elements or select these activatable elements using an input device, such as a mouse, keyboard, touchscreen, or the like, to activate the components. The display 806 may include a help element 902 that may be activated to obtain help information regarding use of the housing. It may also contain real time project or process plans. It may also include "how to" assistance including videos related to the various projects, stages, processes, and tasks performed at the project location. The user interface on the display 806 may also include a call center activatable element 904. Selection of the call center activatable element 904 may cause a call to be initiated with a call center so that the individual using the system 100 may have a telephone and or video conference with personnel at the call center. The user interface on display 806 may also include a tutorial activatable element 906. Selection of the tutorial activatable element 224 causes a tutorial to be displayed to teach the individual about operation of the housing.

Shipping or delivery company personnel may activate the delivery activatable element 908 (FIG. 9). This causes a delivery functionality to be displayed where delivery notes may be added and where information may be gathered from the delivery person regarding a particular delivery.

An inspector activatable element 912, may be activated to cause the inspector functionality to be activated. The inspector functionality may enable an inspector to add inspection notes, provide electronic inspection certificates and the like. The system can provide reports that can be automatically generated from the existing data described herein as well as notes manually added during the construction process. The reports can be generated at predetermined times such as daily or upon completion of specific tasks.

Figure 11:
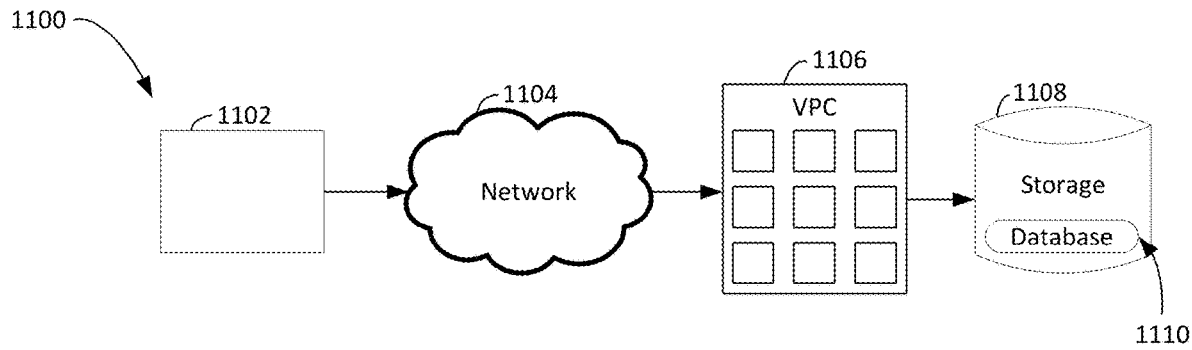
FIG. 11 is a schematic of aspects of the invention.

As shown in FIG. 11, the exemplary embodiments may be implemented in a decentralized computing environment 1100, that may include distributed systems and cloud computing. FIG. 11 shows one or more systems 1102 that may be in communication with a remote cluster 1106 via a network 1104. The cluster 1106 may store information received from the system 1102 and provide added computational functionality. The network may be a wired network or a wireless network or a combination thereof. The network 1104 may be a secure internet connection extending between the system 1102 and the cluster 1106, such as a virtual private cloud (VPC). The server may be a computing device and can be in communications with the site computer device. The cluster 1106 may include access to storage 1108. The storage 1108 may include a database 1110 in which information regarding a project location is stored in a consistent manner.

Figure 12:
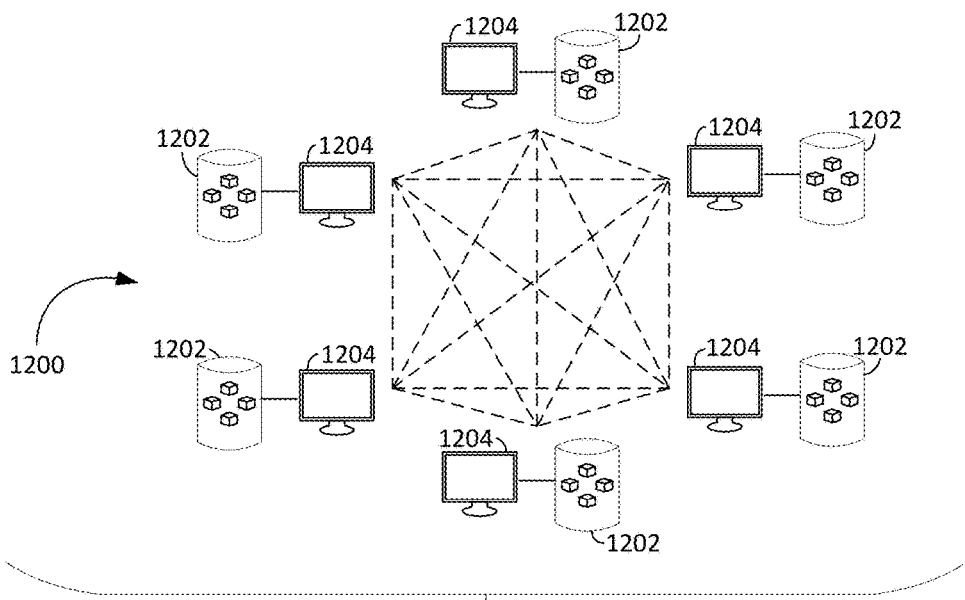
FIG. 12 is a schematic of aspects of the invention.

FIG. 12 shows diagram 1200 of an example of a peer-based network where an immutable storage 1202 is broadcast and shared among the nodes 1204. This network may be resident in the VPC cluster 1106 (FIG. 11) or in the network 1104 for example. The nodes 1204 may represent computing resources, such as server computer systems or other computing systems, residents at the parties identified in FIG. 12, for example. Each node that has access to a copy of the immutable storage 1202.

Figure 13A:
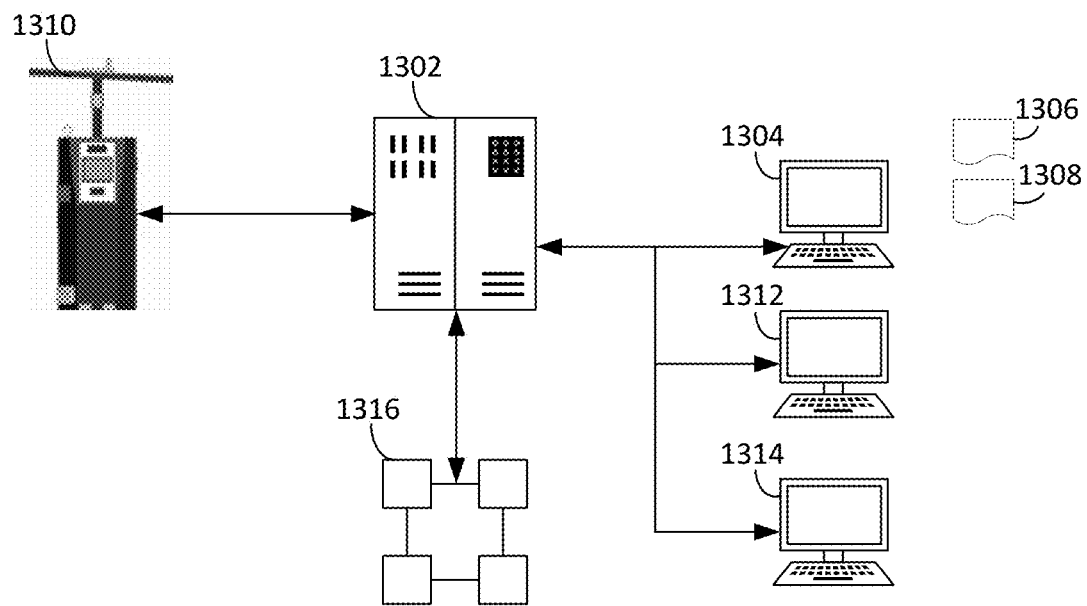
FIG. 13A is a schematic of aspects of the invention.
Figure 13B:
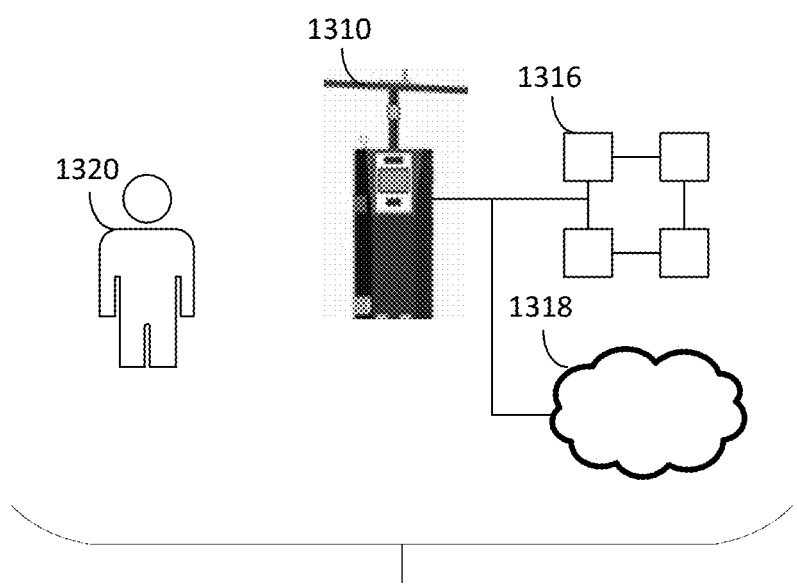
FIG. 13B is a schematic of aspects of the invention.

Referring to FIGS. 13A and 13B, a computerized system 1302 can be in communications with a local computerized system 1310 such as a kiosk. The various computer devices, including the server and site computer device (e.g., system, controller, and any combination), can be in communications with immutable storage 1316. External computer systems having external data such as a shipping computer system 1304, manufacturing computer system 1312, regulatory computer systems, government computer systems, weather computer systems, enterprise computer systems, public computer systems, customer computer system 1314 or other external or third-party computer systems having external data can be in communication with the system and the immutable storage. The external data can be associated with a date, time, locations, individual, business, physical object, event, activity and any combination.

Orders such as 1306 can be created and processed as well as other activity 1308 such as transactions and processes. The immutable storage can include a distributed ledger, immutable database, block-chain structure, and the like. The communications between the various computer device, including the server and the site computer device and immutable storage can be a global communications network 1318, wide area network 1316, or local area network, delivered to a computer readable medium from one device to another (e.g., USB drive, CD, DVD) and can be wired or wireless.

Figure 14:
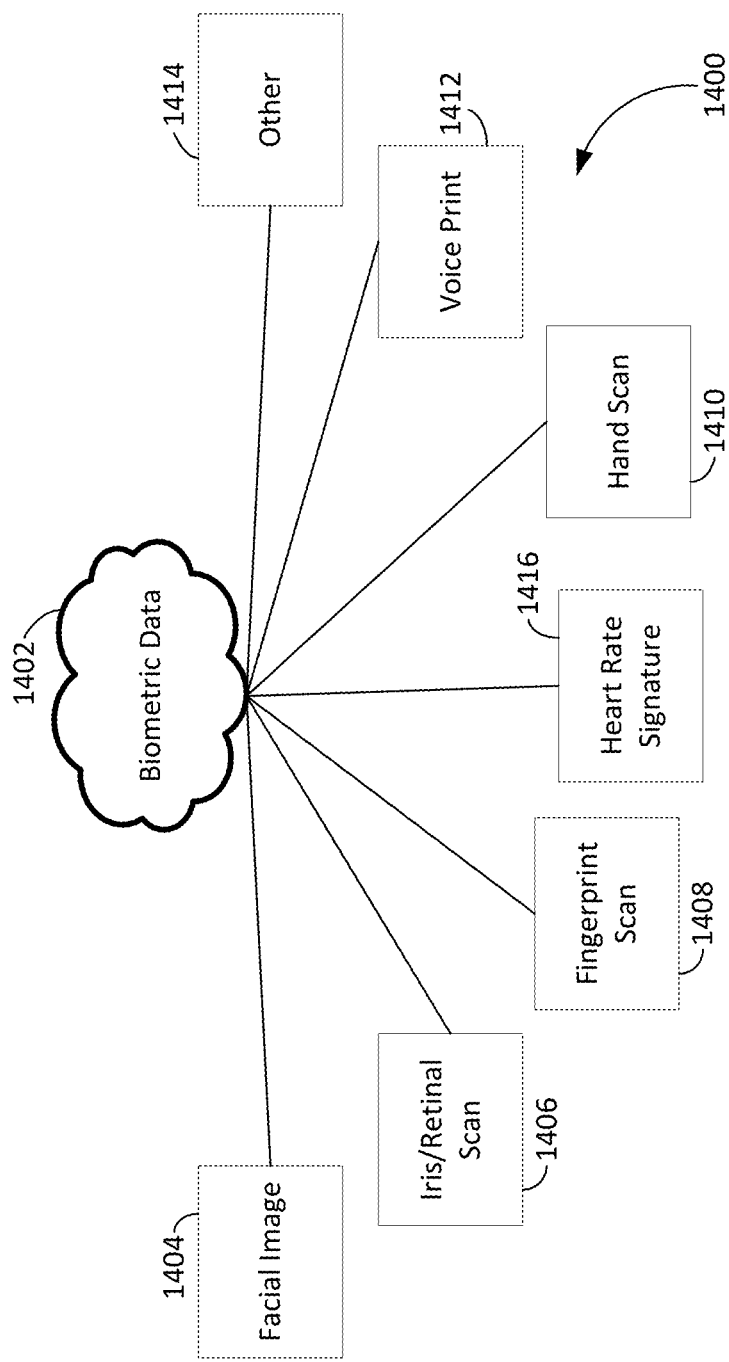
FIG. 14 is a schematic of aspects of the invention.

FIG. 14 shows a diagram 1400 that illustrates various types of biometric data 1402 that may be obtained by biometric-based identification devices at the project location to attempt to identify individuals. Biometric data may include facial recognition 1404, an iris/retinal scan 1406, a fingerprint scan 1410, a hand scan 1410, a voice print 1412 or heart rate signature 1416. It should be noted that other types 1414 of biometric data may also be used in exemplary embodiments to help identify individuals uniquely. Also, an individual may be required to provide multiple types of biometric data in some instances.

Figure 15A:
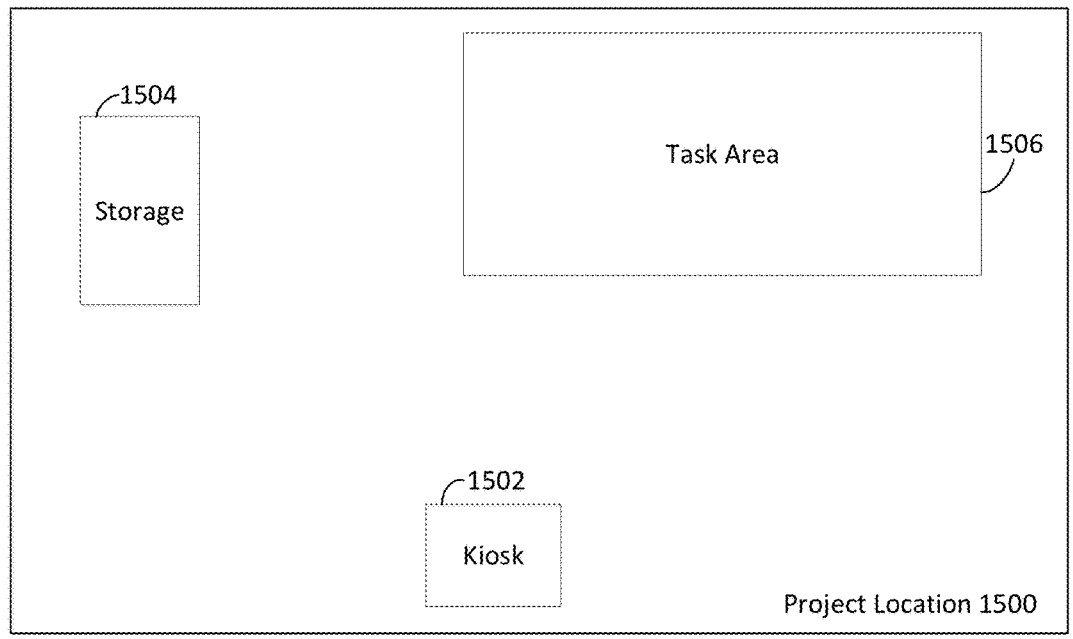
FIG. 15A is a schematic of aspects of the invention.

To help illustrate an example of geofencing, FIG. 15A shows an illustrative project location 1500. The project location 1500 may include a housing 1502 for the system as well as storage location 1504 that can be a building, trailer, shed or the like. The storage location 1504 may hold tools, equipment, wearables and/or materials. The project location 1500 may also include a task location 1506. The task location may be where tasks are performed using materials to produce a good or offer a service.

Figure 15B:
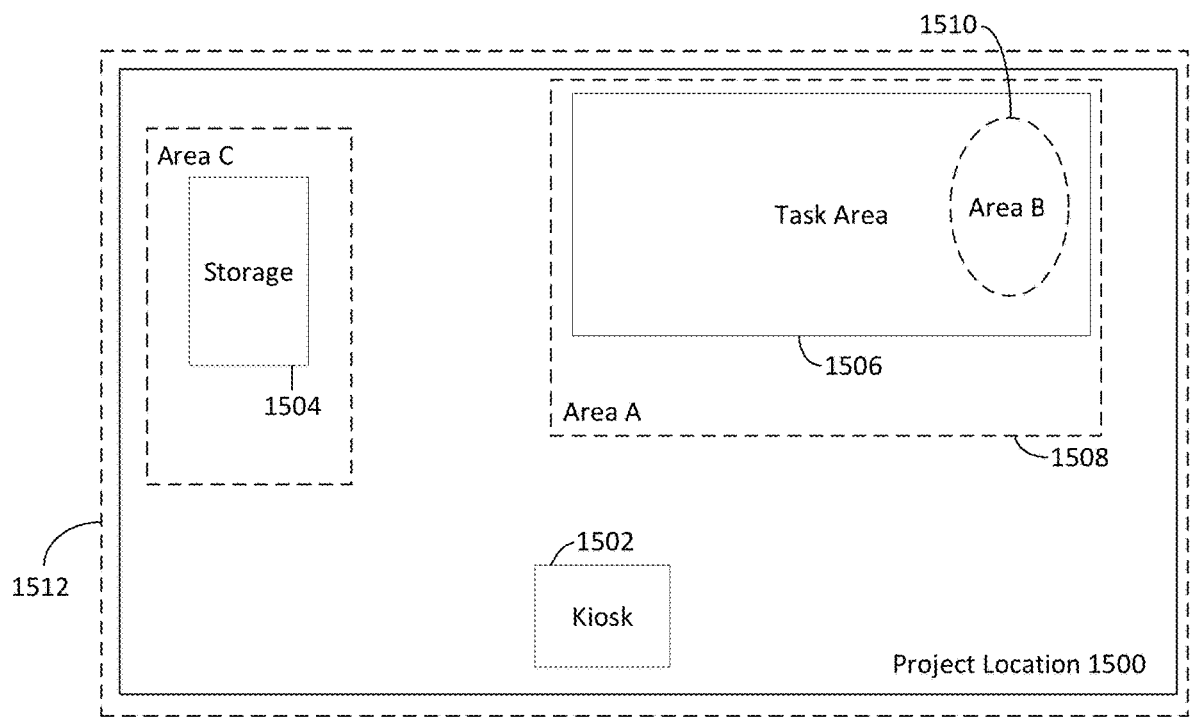
FIG. 15B is a schematic of aspects of the invention.

FIG. 15B shows an example of different areas that may be established for geofencing at the project location 1500. Area A shown a boundary 1508 may include the entirety of the project that is under construction 1506. Area B 1510 may be a portion of the project, such as the kitchen. Another area may be a shed and another area may be the entire project location. Individuals may have access to none of these areas or to a subset of these areas, including all areas.

Figure 16:
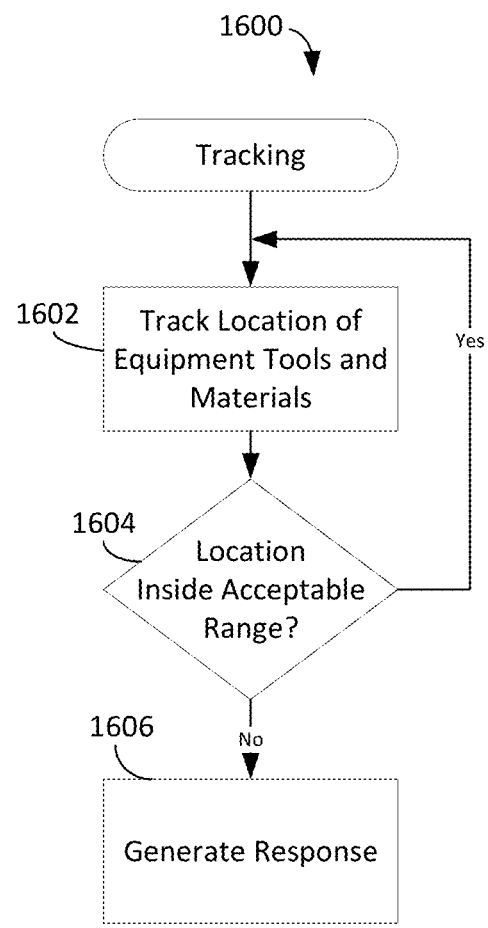
FIG. 16 is a flowchart of aspects of the invention.

Referring to FIG. 16, the system may track the location of equipment, tools, or materials at the project location 1602. The system can check whether the location of the equipment, tools or materials is acceptable or not 1604. For example, suppose that lumber has been delivered to the project location and the location of the lumber indicates that the lumber is removed from the project location. This would be problematic and would warrant a response. If the location is not acceptable as checked in 1604, a response is generated in 1606.

The system helps manage deliveries an illustrated in FIG. 17 that depicts a flowchart 1700 showing steps that may be performed in this regard regarding deliveries. Initially, the identity of the delivery person is received, recorded, confirmed or otherwise processed and can be used to indicate that the delivery person is the appropriate party and is permitted access to the project location 1702. In addition, information may be entered by the delivery person using the housing, such as by entering information via screen 408 (FIG. 4A) 1704. The location of delivery, the date of delivery, the time of the delivery, the quantity of the delivery, the identity of the delivery person and the weather may be recorded as part of the information that is kept regarding the delivery. This information can be used to track and confirm deliveries as well as to understand the conditions when the delivery was made.

FIG. 18 shows a flowchart 1800 of steps that may be performed when image capture devices, such as still cameras or video cameras, from multiple adjacently situated systems are used in conjunction in one example application. Video feeds or still images may be obtained from the image capture devices from multiple systems 1802. The video feeds or images may then be processed, such as by the cluster described above, using software such as motion detection software, thermal image analysis or other image analysis software to identify activity that may warrant a response 1804. When a motion is detected, it can trigger data capture for that event.

The information obtained may be stored on or referenced from immutable storage 1806. The information may be stored on an ongoing fashion, in databases as described below, and may be referenced in an immutable persistent fashion on the storage. This information may help resolve disputes between parties involved on the project or process. For example, suppose the assembler asserts that the wrong items were delivered. Since there is a complete record references on the immutable storage of all deliveries, these records may be accessed to resolve the dispute. Insurance providers may access injury records referenced on the immutable storage to settle or confirm claims. Disputes regarding pay among workers may be resolved by checking the recorded hours on site to determine the appropriate pay for the workers. Inspection records may be accessed to confirm that proper inspections were carried out and passed.

The information referenced in the immutable storage may also be accessed from a computing device of an owner, end user, customer, integrated and the like at 1808. The computing device may be, for example, part of a home maintenance system that manages and controls home systems, such as heating, air conditioning, lighting, an alarm system, or the like. The computing device may be part of a smart home controller and may interface with appliances and other items that are interconnected via a home control network. The computing device may include a document management system for securely storing the transferred information. The computing device may be a facilities management system, or operations system associated with the project location.

There can be a relationship between the smart contracts and the project schedule. Steps performed relating a process, transaction or activity can be used to trigger all or part of a smart contracts. Based on an event, smart contracts may be constructed that use the immutable storage for contractual arrangements associated with the transaction, process, or activity. The smart contracts can be implemented in software and can be used to provide electronic payments to parties for activities relating to the events using, for example, electronic payments, crypto currencies, fiat currencies and other forms of payments. The smart contracts may specify the conditions required for payment and may specify the amounts of payment.

Smart contracts may also play a role with deliveries. First, delivery and/or materials information can be obtained regarding delivery to the project location or to an individual. The information obtained can include if the materials delivered match the material requirement record, manufacturer, and/or supplier which can be confirmed by multiple parties. The information can also be the individual that delivers material or receive material. The information can be the individual that is a party to a transaction. The information can be the individual that participates in a process or activity.

A smart contract can be provided that uses the immutable storage. A determination is made whether the conditions specified in the smart contract are satisfied by an event that can include a transaction, process or other activity. If the conditions are satisfied, electronic payment for the delivery can be realized. If the conditions are not satisfied, notice of outstanding issues are sent and an individual or computer system may attempt to remedy the issues. The process may then repeat until the conditions of the smart contract are satisfied or some event termination the attempts occurs, such as a pre-determined number of remedies are tried.

To pair an individual its virtual representation, and with material, the system captures events at various points of a transaction, process or activity associated with the individual. Pairing the individual with the virtual representation can include several elements or components. Included in the pairing process can be the physical observation of the individual and then associate the individual with a virtual representation so that the individual is properly associated with the virtual representation. This verification provides data that the virtual representation is accurately associated with the individual as a factor rather than simply trusting that the virtual representation is accurate. This system can use manual or automated processes to physically observe the individual and associate the individual with the virtual representation during various events of a transaction, process, or activity. Verification can also use the metadata that is associated with the interaction of physical items by individuals and electronics when the item is created, transported, installed, activated, and destroyed. The metadata that can be captured and placed into immutable storage can provide stakeholders an audit trail of history for their physical asset using a verified paired virtual representation.

For example, when raw material is harvested, a harvesting record can be created that captures the individual preforming the harvesting and can include metadata concerning the event and verification that the raw material is associated with the harvesting record. For example, a digital image of the individual and the raw material can be captured, and the images and its metadata of the image captured can be included in the virtual representation. For example, a sensor having a GPS transponder, camera and transceiver can be used to capture the individual and harvesting event. The metadata of the individual and harvesting event can include date, time, location (e.g., GPS coordinates), harvesting image, harvesting entity, harvesting equipment and any combination. Once harvested, raw material can be loaded on a transport (e.g., vehicle, plane, ship, and the like) by the same of difference individual. By capturing the individual and the harvesting event and verifying that the individual and raw material and the virtual representation(s) are paired, and stored on the immutable storage, the individual, physical material and the virtual representation are paired allowing for reliance upon the digital record to accurately represent the event. Harvested material may also include a tag of other indicium that, when scanned, can be included in the stored record to provide for an audit trail and multiple stored records with the indicium are included in the persistent storage.

Because verifications using these streams are chronological, altering the information could require alteration of the metadata prior to and after the altered record. Therefore, the altered record would be inconsistent with the associated records potentially both temporally and geographically and an attempt to alter the record would be discovered. In one example, the metadata taken from the harvesting and transportation can provide data which can be used to determine a range of acceptable travel times. If a travel time is recorded outside a predetermined acceptable range of metadata, it can indicate tampering with the data, incorrect capture devices or other abnormalities that can need correcting.

The use of an immutable storage further reduces the risk of alterations of records as well as increasing the verification of information. Further, pairing assets associated with the event, involving the asset, interactions with the asset and the associated metadata provide for a substantiated digital asset, reduce, or eliminate risk and improve capital efficiency. Further, the pairing of assets facilitates commerce by allowing electronic transactions with assurances that the virtual representation used in the electronic transaction is paired with the physical asset.

Verification, including verification of an individual, can include verifying that the individual and the virtual representation match and can be accomplished in a variation of methods including interaction with identification elements such as biometrics, a tag, label, and the like, capturing an image of the individual, capturing a video of the individual, capturing indicia such as a tag affixed or otherwise associated with the individual, human visual inspection, biometrics, at and between events, capturing the dimensions of the individual at and between events, and any combination. Identification of an individual performing or otherwise associated with an event can be captured by identification devices (e.g., cards, tags, RF ID. smart dust, beacons) and biometrics including visual capture (e.g., facial recognition), voice recognition, iris scan, fingerprint, palm print and any combination.

The system can retrieve the harvesting record, receive verification that the raw material delivered to a shipper is the same that was harvested and create a shipping record. The metadata associated with delivering the raw material to the shipper can be captured and included in the shipping record. The shipping record can include information about the shipper and the individual delivering the raw material to the shipper. The shipping record can include information about the destination of the raw material. By capturing the shipping event and verifying that the raw material harvest delivered to the shipper and the virtual representation are paired, and stored on the immutable storage, the physical material and the virtual representation are paired from harvesting the delivery to the shipper allowing for reliance upon the digital record to accurately represent the physical material and its disposition.

The system can retrieve the shipping record, receive verification that the raw material delivered by the shipper to a processor (e.g., manufacturer), is the same that was harvested, shipped, and received. The metadata associated with delivering the raw material to the processor can be captured and included in a delivery record. The delivery record can include information about the shipper, processor, worker, and any combination. The delivery record can include information about the processor, location, and other information. By capturing the delivery event, including the associated individual, and verifying that the raw material harvest delivered to the processor by the individual and the virtual representation are paired, and stored on the immutable storage, the individual and the virtual representation are paired from harvesting the delivery to the processor allowing for reliance upon the digital record to accurately represent the individual throughout the process.

Once the processor processes the raw material to form a processes material, the system can create a processor record including that the raw material delivered to the processor is integrated into a processed material and is the same raw material that was harvested, shipped, and received. The metadata associated with processing the raw material can be captured and included in a processing record. The processing record can include information about the harvesting, shipping, processor, individual (e.g., worker), and any combination. By capturing the processing event and verifying that the raw material harvested delivered to the processor and the virtual representation are paired, and stored on the immutable storage, the physical material and the virtual representation are paired from harvesting to processing allowing for reliance upon the digital record to accurately represent the physical material and its disposition.

Figure 19A:
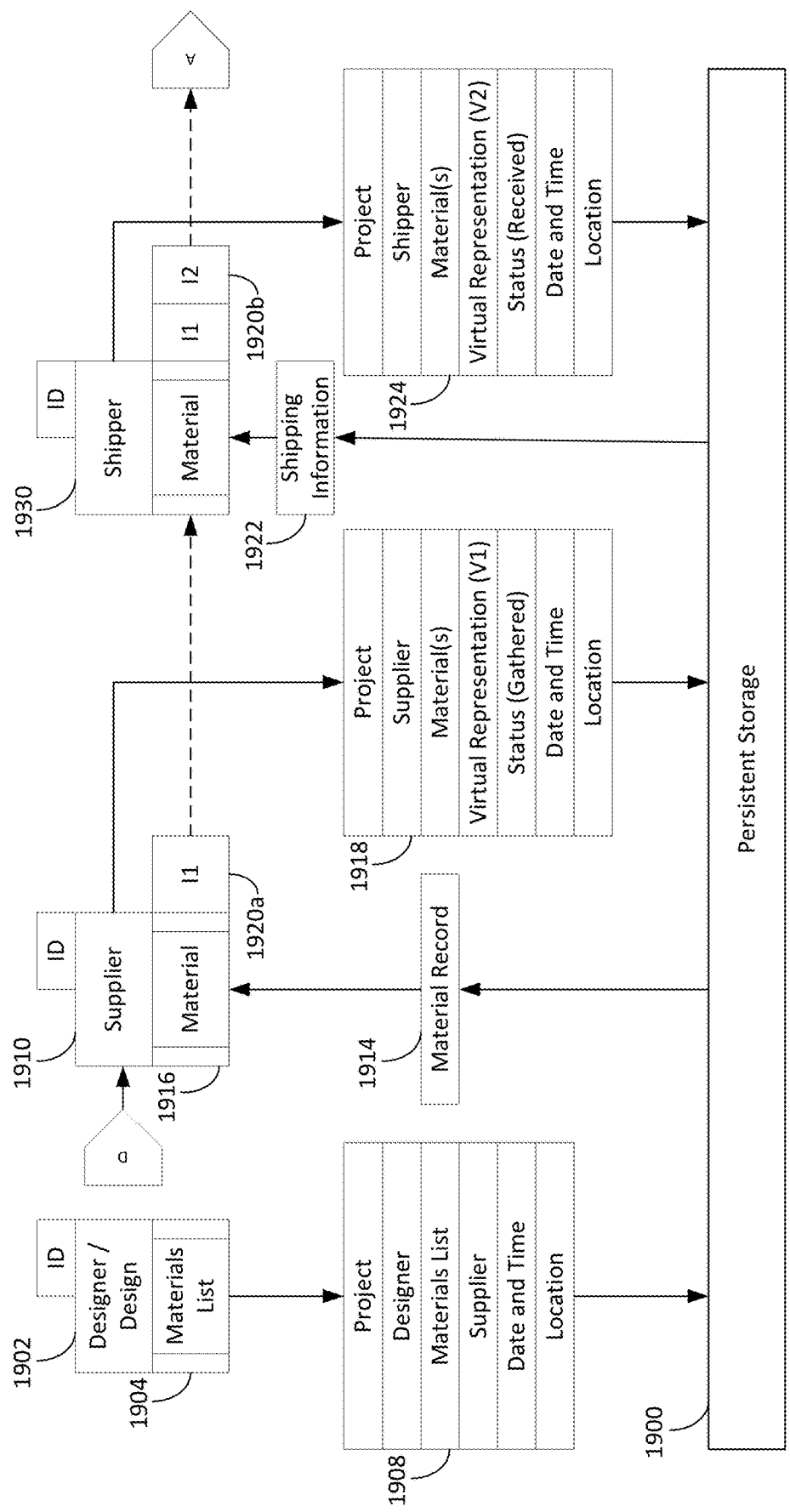
FIG. 19A is a flowchart of aspects of the invention.

Referring to FIG. 19A, a user of the supplier computer system 1910, can select or otherwise acquire an object such as material 1916 identified on the material list from a materials requirement record or designer record that can be retrieved or otherwise received by the supplier computer system from the immutable storage. The supplier can verify that the material matches the material requirement record, and the system can capture this event. For example, one method of associating the physical material with a virtual representation is using a indicia 1920a ($I_1$) placed on the material. The indicia is then physically verified to be associated with the material from the material list or the material requirement record. Therefore, the physical material and the virtual representation ($V_1$) are paired by recording this event and associating the physical material, $I_1$, and $V_1$. In one embodiment, the indicia can include the following information:

| Description | Digits | Information |
| --- | --- | --- |
| Locations | 19-20 | GPS XX.XXXXXX XXX.XXXXXX |
| User ID | 12 | SSN XXXX + Initials XX + ID XXXXXX |
| Date | 10 | XX/XX/XXXX |
| Time | 7 | Zulu XXXX:XX |
| Material | 12 | UPC/Barcode XXXXXXXXXXXX |

An event record such as a supplier record 1918 can be created and stored on the immutable storage. The capture event can include a unique number and include the supplier ID, date and time, location, material ID, status, and any combination. The material ID can be from an original manufacturer or the supplier. The status can include that the material has been gathered, packaged, ordered, is in stock or on back order, shipping information and any combination. The shipping information can include the origin, destination, shipping instructions, shipper, and any combination.

Figure 19B:
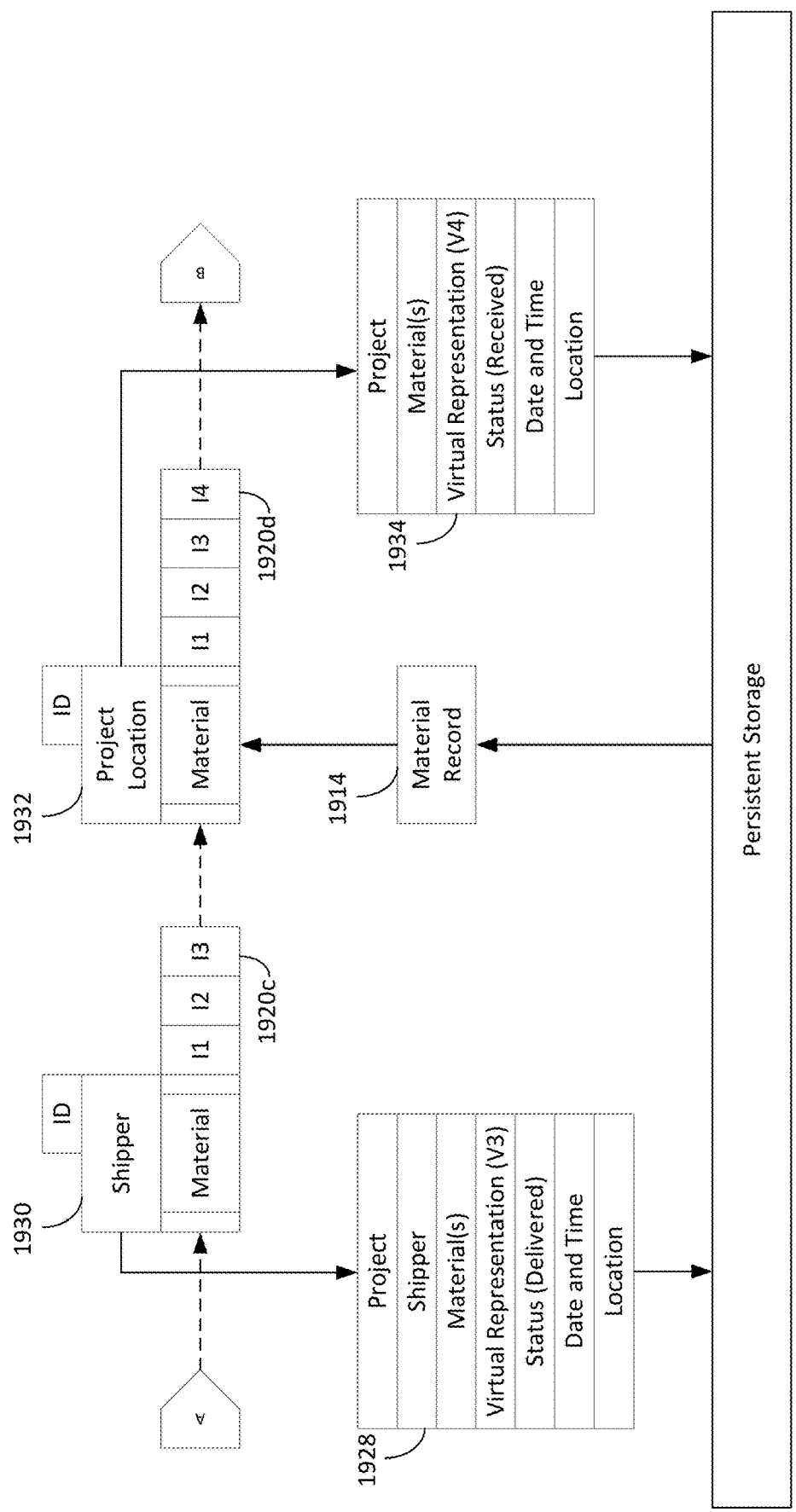
FIG. 19B is a flowchart of aspects of the invention.

Referring to FIG. 19B, a shipper can retrieve shipping information or a hash of the shipping information from the immutable storage 1922 identifying the material location, load, destination, pick time, delivery time, and other information concerning the shipping of the materials. The shipper can verify that the physical materials being retrieved from the supplier match the virtual representation of the supplier record using the associated data or a hash of the data. If the materials are verified, the shipper can physically capture the event, for example, by affixing its indicia 1920b ($I_2$) to the materials representing this verification. A supplier shipping pickup record 1924 can be created and stored on the immutable storage. The supplier shipping pickup record can include project, shipper, material, status, date, time, location, and any combination. The mode of transportation of the material can also be tracked and stored on the immutable storage. For example, if the shipper uses a vehicle, the date, time, location, and other metadata associated with the vehicle can be gathered along the route and stored on the immutable storage. Verification can be provided using the metadata of the various events. For example, if the date, time, and location of the supplier record is within a certain range of values of the date, time and location of the supplier shipping pickup record, there will be verification that the proper materials were physically transmitted from the supplier to the shipper.

In one embodiment, the metadata can be added to a hash where the hash is the results of the metadata reduced to a fixed length value. The next time that the record is retrieved, that hash can be divided inti discrete data points that can be stored locally so that the hash may not be publicly exposed. The hash that is stored on the immutable storage can include a pointer to the local storage and compared with one or more discrete points.

The shipper can deliver the material to the destination such as a project location. When the shipper delivers the materials to the project location, the shipper can capture this event by creating a supplier shipping delivery 1928 record using a shipper computer system 1930. The shipper can verify the event by methods including adding a indicia 1920c ($I_3$) representing that the proper materials were delivered to the proper location. The project location computer system 1932 can be used to verify that the materials were properly delivered by retrieving the material record 1914 from the immutable storage and using the record to match the physical materials delivered. In one embodiment, the shipper can use the tags that are part of the virtual representation to match 13 with the material and the information stored on the immutable storage to capture and verify the event. When the material is delivered, the project location can use a project computer system 1932 to retrieve the material record from the immutable storage and match the material delivered with the material record. The project location can add an indicia 1920d ($I_4$) to the material to capture this event. The project location can create a project location material received record 1934 that can include the project, material, virtual representation ($V_4$), status, date, time, location, other metadata, and any combination. The shipper, worker at the project location, or both can physically inspect the material and verify that it is matches the virtual representation stored on the immutable storage. This verification can be included in the information that is stored on the immutable storage by the shipper and a worker or system at the project location.

Figure 19C:
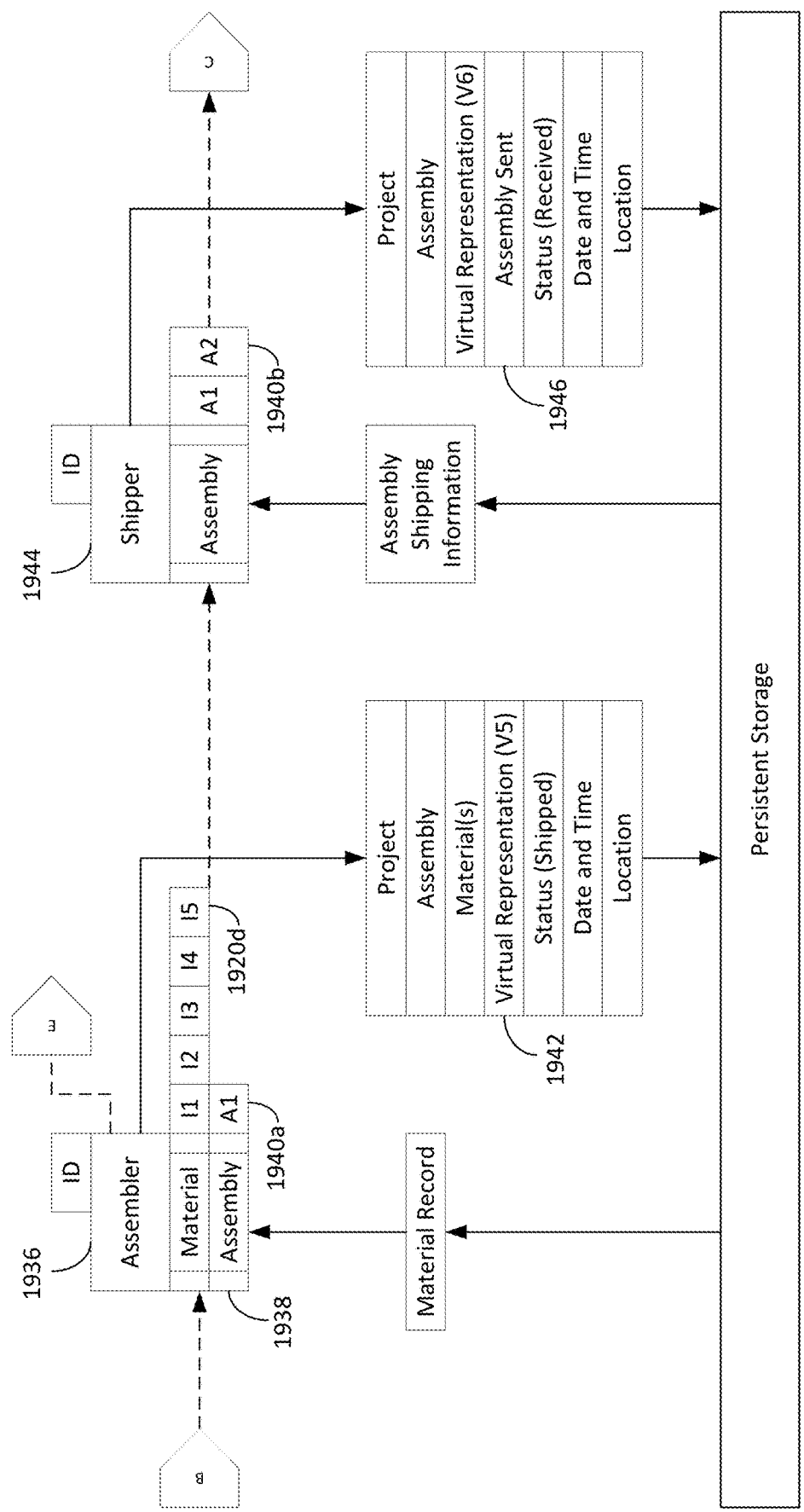
FIG. 19C is a flowchart of aspects of the invention.

Referring to FIG. 19C, the project location can be an assembler, or the assembler can be at a separate location from the project. For example, in the manufacturing of a vehicle, the project location can be the assembly line for the vehicle and multiple assembly locations can be involved. The main assembly line can be the project location and the assembler can be a component or sub-component of the manufacturing process. This system can be used for the project, or sub-project that are included in the overall project. Further a sub-project can be treated as a project as discussed herein.

An assembler computer system 1936 can be used to retrieve the material record from the immutable storage. The material record can be used to match the materials delivered to the assembler to verify that the proper materials were received by the assembler. The assembler can add indicia 1920d ($I_5$) to the material, or use other verification methods described herein, to capture the event. The assembler can also capture the material used and the assembly 1938 by adding a indicia 1940a ($A_1$) to the assembly. An assembler record 1942 can be created and stored on the immutable storage. The assembler record can include the project, assembly description and other information, assembler, material(s) used, virtual representation, shipping information date, time, location of the assembly, other metadata, and any combination.

One verification can be the comparison of an image of the physical object taken at the first event and the image of the physical object taken at the second event. In one embodiment, the determination if the two images represent the same physical object can be made by comparison the distance between the images. The distance between the images of the two object captures do not have to be identical but can be defined by the "closeness" between the images. In one embodiment, the distance can use the Euclidean distance between the $l^{th}$ and $j^{th}$ physical object. Distance between the p-dimensional vectors can be represented as:

$$d_E(i,j) = \sqrt{(\Sigma_{k=1}^{p}(x_{ik}-x_{jk})^2)} \tag{1}$$

or by using the weighted Euclidean distance that can be represented as:

$$d_E(i,j) = \sqrt{(\Sigma_{k=1}^{p} w_k (x_{ik}-x_{jk})^2)} \tag{2}$$

Where $d_E$=distance, i=first image, j=second image, and w=weight between kth measure which can be subject to the following $$0 < w_i < 1 \text{ and } \Sigma_{i=1}^{n} 1 \tag{3}$$

In one embodiment, the verification process can include an individual retrieving the first image of the physical object and comparing the first image with the physical object in proximity of the individual. The individual can review the first event record and the second event record to also make a determination of the physical object has remained the same from the first event to the second event. Information. In one embodiment, multiple individual and computer system can make the comparison. The comparison can also be crowd sourced so that multiple verifications are made from an individual, computer system and any combination.

The comparison can be between a first image of an individual and a second image of a physical object. The first image metadata can be compared with the second image metadata and a determination can be made if the individual and the physical object were in proximity and if so, when and for hoe long. The comparison of the first image to the second image can include a comparison of the backgrounds contained in each image to determine if the environment where the first image is capture is consistent with the environment fo the second image. If so, the confidence that the individual and the physical object were disposed at the same location increases.

Once completed, the assembly may need to be delivered to another location. The assembler record can include shipping information, or an assembly shipping record can be created and stored on the persistent record. If the assembly needs to be delivered, a second shipper can use a second shipper computer system 1944 to retrieve the shipping record, assembler record or other shipping information that is used to identify the origin, locations, assembly, pick up time, delivery time and other information associated with the transportation of the assembly from one location to another. The assembly can be received by the second shipper and the second shipper can capture the event such as with a indicia 1940b ($A_2$) to the assembly representing that the assembly has been verified by the second shipper as properly provided and received by the shipper. A second shipper pick up record 1946 can be created and stored on the immutable storage.

Figure 19D:
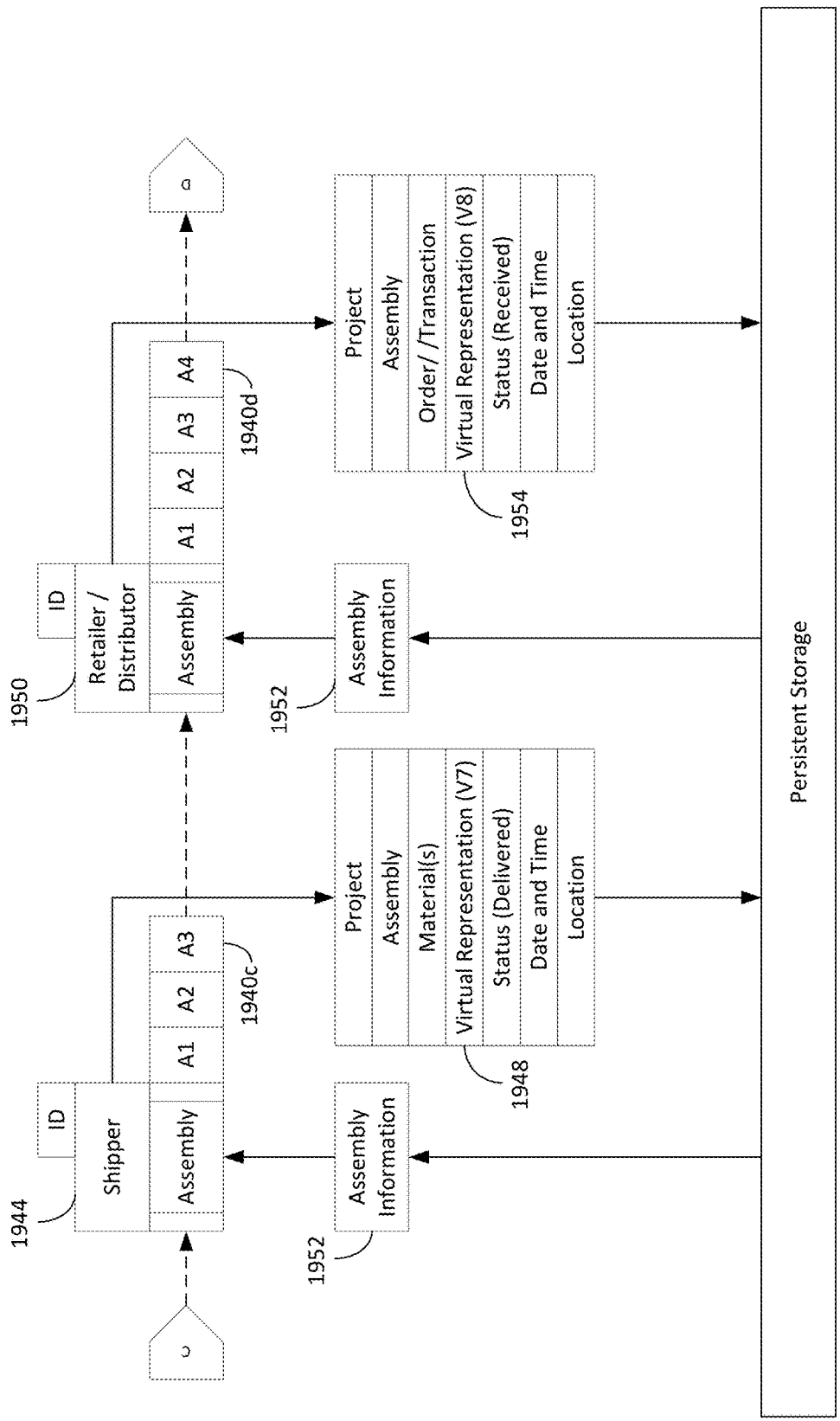
FIG. 19D is a flowchart of aspects of the invention; and,
FIG. 19E is a flowchart of aspects of the invention.

Referring to FIG. 19D, the second shipper can deliver the assembly to a retailer, distributor, or customer. The assembly can be a component to be further used or a final product. When the second shipper delivers the assembly to a retailer or distributor, the second shipper can create a second shipper delivery record 1948 using a second shipper computer system 1944. The second shipper can capture the event such as using a indicia 1940c ($A_3$) representing that the proper assembly was delivered to the proper location. The second shipper can use the verifications that are part of the virtual representation to match $A_3$ with the material and the information stored on the immutable storage.

The retailer or distributor computer system 1950 can be used to verify that the materials were properly delivered by retrieving the assembly record 1952 or second shipper record 1948 from the immutable storage and using the record to match the physical assembly delivered. The retailer or distributor can capture the event and can add a indicia

1940d ($A_4$) representing that the proper assembly was received at the proper location. A retailer distributor record 1954 can be created and stored on the immutable storage.

Figure 19E:
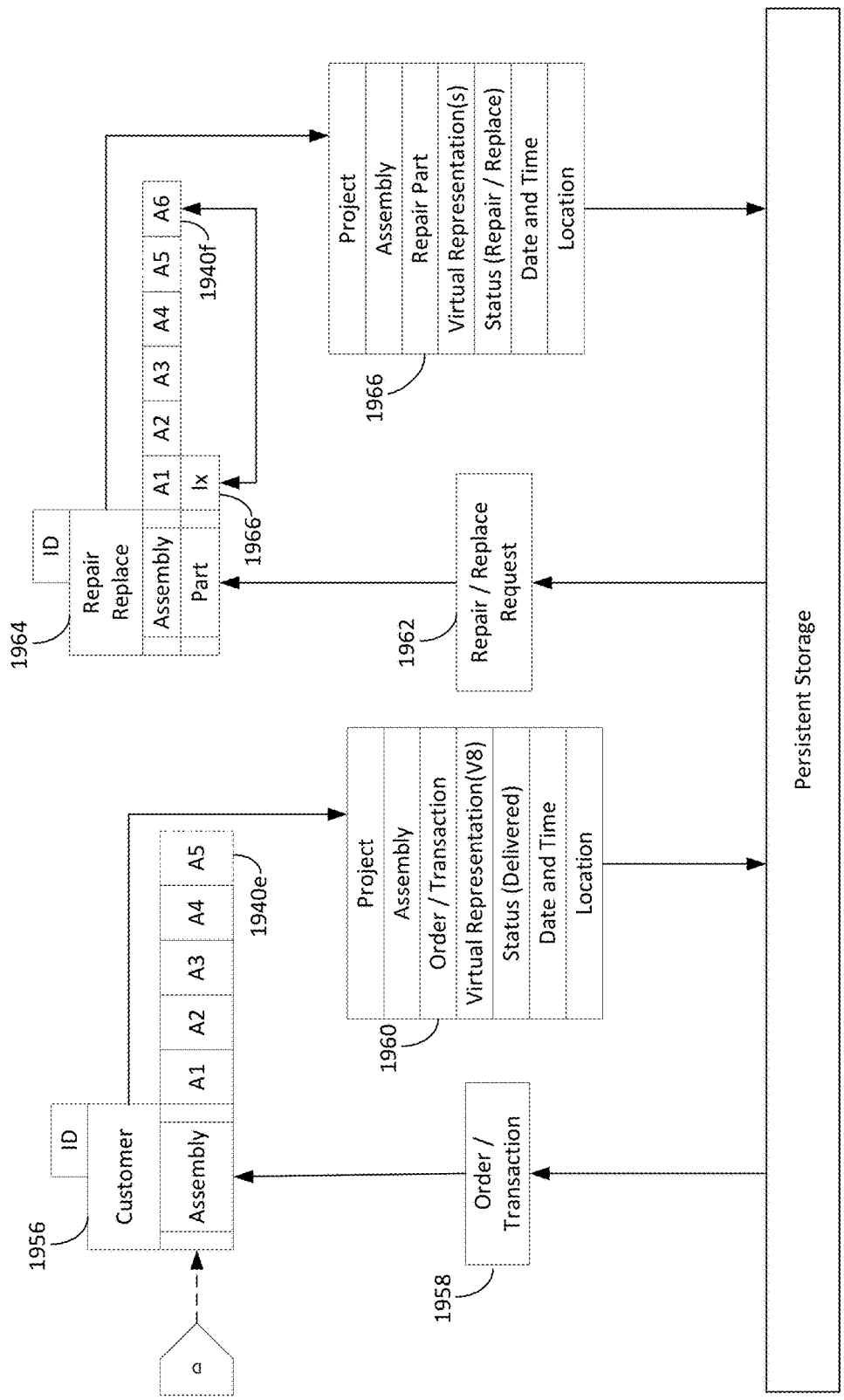

Referring to FIG. 19E, a customer can receive the assembly as using a customer computer system 1956 to retrieve or otherwise receive an order record 1958 from the immutable storage or other system requesting that a customer receive the assembly. The customer can be shipped the assembly using the system as described herein with a shipper performing the steps and the system performing the steps associated with the shipper and second shipper above. A third shipper can create a third shipper pickup and delivery record that can be stored on the immutable storage verifying that the assembly was properly provided from the realtor or distributer to the customer. The customer may capture the event and can add a indicia 1940e ($A_5$) to the assembly that can be associated with the virtual representation ($V_8$). A customer record 1960 can be stored on the immutable storage.

Using this system, the customer can be assured that the assembly was independently verified and authenticated from the design to the delivery to the customer and that the virtual representation of the assembly and its components (e.g., materials) are paired.

In one embodiment, a repair request 1962 can be created and stored on the persistent storage. The repair request can be associated with the assembly and retrieved by a repair computer system 1964. The repair company can receive a part using the system described herein, perform a repair or replacement action, and capture the event such as by using a indicia 1940f ($A_6$) to the assembly indicating that the assembly has had a part repaired or replaced. The repair part can also have a preexisting indicium from the use of the system herein and the repair company can capture the event such as by using a indicium 1968 (Ix). A repair record 1966 can be created and stored on the immutable storage.

The system described herein can pair the physical material and/or assembly with a virtual representation. Failure to pair the physical material or assembly with the virtual representation can negatively impact areas such as regulatory requirements. Regulatory requirements are a set of rules that can specify the standards for a project. Regulatory requirements impact designs, materials, worker's license and experience the project and process. For example, a building code may require that construction materials be installed in accordance with manufacturer's specifications and warranty regulations. Failure to follow the building codes can result in the project not being approved, errors, lack of customer satisfaction, insurance claims, injury, litigation, and other negative ramifications. Tracking, management, and verification of materials to ensure compliance with regulatory requirements and proper installation according to applicable specifications is an important aspect to many projects and processes. Tracking and record keeping during the project or process can be beneficial, as it can be difficult to perform these tasks after project or process completion because the materials can be hidden from view or otherwise inaccessible. For example, electrical wiring in a project or process can be hidden behind walls and ceilings once the project is complete.

Systems at multiple locations may be interconnected using image capture devices, RFID, QR codes, barcodes, biometric scanners, still cameras, video cameras, Bluetooth scanner, and the like to identify individuals or machines that are performing verifications during the process. Further, multiple individuals or machines are performing verifications so that there is not a reliance upon any one entity for verifications. The processing of capturing data, including images, from the multiple systems at multiple locations can be used to improve the verification of proper materials and assemblies as well as to pair the physical items with the virtual representation.

Verification of processes, inspections, completions and deliveries with adjustments and notifications (manual and automated) with confirmation would ensure increased productivity, especially if accessible in real time at the location. Real time processes and procedures planned with corresponding training and manuals would improve quality control and efficiency. This has been a long felt need in the prior art that has not been satisfied with a controller that is uniquely associated with an asset location.

Automated verification of quantities, quality, and correct product deliveries along with after delivery tracking of materials with accountability is seldom used. Designated delivery areas with geofenced control and tracking of materials once delivered would help prevent loss. Confirmation of products integrated at the asset location provides transparency regarding sourcing, warranties, as well as future reference during the structure and individual product's life of use.

By using the various tags and virtual representations, each entity in the process can verify that the physical materials match any record the precedes that entity.

This process can include internal and external individuals and machines for performing inspections (e.g., verifications). For example, the system can receive a set of internal inspection information entered into the system from an internal inspector representing an internal physical inspection of the project, material or assembly. As the items travel, an internal inspector can provide inspection information representing the stages of the project. The system can also receive a set of external inspection information from an external inspector and an external inspection computer device representing a third-party physical inspection of the project at predetermined stages of the project. Based upon the internal inspection, external inspection or both, an inspection record can be created and stored on the immutable storage.

The verified pairing described herein can also be used to verifiable pair physical assets with installation instructions, storage instructions, warranties, ownership, service, maintenance, and any combination thereof.

The system can also facilitate the use of digital wallets. The information that is contained on the digital wallet can be paired with a physical object so that transactions associated with the physical object can be conducted with verification that the digital representation in the digital wallet represents the physical object, whether the physical object is fungible or unique.

What is claimed is:

1. A computerized system for verifiably pairing an in individual with a digital representation comprising:
    a computer system in communication with an immutable storage;
    a first data capture device in communications with the computer system;
    a second data capture device in communication with the computer system;
    a set of computer readable instructions included in the computer system configured for:
        creating a first event record from the first data capture device including, a first location, a first time and a first set of metadata wherein the first set of metadata includes a first digital representation of a first individual captured by the first data capture device, creating a subsequent event record from the second data capture device including a second location, a second time and a second set of metadata wherein the second set of metadata includes a subsequent digital representation captured by the second data capture device of a second individual, comparing the first set of metadata to the second set of metadata, and, storing the first event record and the subsequent event record on the immutable storage.

2. The computerized system of claim 1 wherein the set of computer readable instructions include instructions for receiving external data from an external data source associated with the first location and comparing the first location and the first event record, generating a comparison information representing that the first location and the first event record are consistent.

3. The computerized system of claim 2 wherein the external data is taken from sources from the group consisting of public records, enterprise software, a local computer device and remote computer device and any combination thereof in communication with the computer system.

4. The computerized system of claim 2 wherein the external data is weather data.

5. The computerized system of claim 4 wherein the weather data includes a position of the sun and set of computer readable instructions include instructions to compare a shadow data with the weather data and the first set of metadata.

6. The computerized system of claim 5 wherein the first individual and the second individual are the same individual and the set of computer readable instructions include instructions for retrieving the first event record and the subsequent event record, calculating a timespan between the first time and the second time and determining that the same individual could travel between the first location and the second location within the timespan.

7. The computerized system of claim 1 wherein the subsequent event record includes a verification data representing that a third individual retrieved the first digital representation of the first individual to verify that the first individual is physically present at the first location.

8. A computerized system for verifiably that individual is associated with an event comprising:

a computer system in communication with an immutable storage;

a set of computer readable instructions included in the computer system configured for:

creating a first event record using a first data capture device wherein the first event record includes a first location, a first time and a first set of metadata wherein the first set of metadata includes a first digital representation of an individual, creating a subsequent event record using a second data capture device wherein the subsequent event record includes a second location, a second time and a second set of metadata wherein the second set of metadata includes a subsequent digital representation of a second individual; and, calculating a timespan between the first time and the second time and calculating that the timespan is consistent with the individual traveling from the first location to the second location.

9. The computerized system of claim 8 wherein the set of computer readable instructions include instructions for determining that the first individual present at the first location is the same individual present at the second location.

10. The computerized system of claim 9 wherein the first event record and the second event record are stored on the immutable storage and are configured to provide an immutable audit record of time, location and activity of the individual.

11. The computerized system of claim 8 wherein the first digital representation of the individual includes a unique biometric identifier.

12. The computerized system of claim 11 wherein the unique biometric identifier is taken from the group consisting of facial recognition, an iris/retinal scan, a fingerprint scan, a hand scan, a voice print, or heart rate signature and any combination.

13. The computerized system of claim 8 wherein the subsequent event record includes a verification data representing that a verifier viewed the first set of metadata and compared it with first digital representation of the first individual and the first individual and that the first digital representation of the individual and first set of metadata are consistent.

14. The computerized system of claim 8 wherein the first event record and the second event record are stored on the immutable storage and are configured to provide an immutable audit record of time, location and activity of the individual.

15. A computerized system for verifiably pairing an individual with a digital representation comprising:

a computer system in communication with an immutable storage;

a data capture device in communications with the computer system;

a set of computer readable instructions included in the computer system configured for:

creating an event record using the data capture device wherein the event record includes an event location, an event time, and a set of event metadata wherein the set of event metadata includes an event digital representation of an individual, receiving external data from an external data source having external location data associated with the event location and comparing the external location data with the event location data.

16. The computerized system of claim 15 wherein the external data includes an external time and the set of computer readable instructions include instructions for determining of the event time and the external time are consistent.

17. The computerized system of claim 15 wherein the external data is taken from sources from the group consisting of public records, enterprise software, a local computer device and remote computer device and any combination thereof.

18. The computerized system of claim 15 wherein the external location data is weather data.

19. The computerized system of claim 18 wherein the weather data includes a position of the sun and comparing a shadow data included in the event metadata is consistent with the weather data.

20. The computerized system of claim 15 wherein:

the event record is a first event record, and the digital representation of an individual is a first digital representation of a first individual; and, wherein the set of computer readable instructions includes instructions for:
- creating a second event record from a second data capture device wherein the second event record includes a second digital representation of a second individual captured by a second data capture device at a second location, and
- comparing the first digital representation of the first individual the second digital representation of the second individual.

21. The computerized system of claim 20 wherein the second event record is stored on the immutable storage and operatively associated with the first event record and configured to provide an immutable audit record of the time and location of the first individual and the second individual.

* * * * *